US008058012B2

(12) United States Patent
Root et al.

(10) Patent No.: US 8,058,012 B2
(45) Date of Patent: Nov. 15, 2011

(54) FIVE-HELIX PROTEIN

(75) Inventors: Michael J. Root, Boston, MA (US);
Michael S. Kay, Somerville, MA (US);
David C. Chan, Arcadia, CA (US);
Peter S. Kim, Lexington, MA (US)

(73) Assignee: Whitehead Institute For Biomedical Research, Cambridge, MA (US)

( * ) Notice: Subject to any disclaimer, the term of this patent is extended or adjusted under 35 U.S.C. 154(b) by 160 days.

(21) Appl. No.: 12/321,300

(22) Filed: Jan. 20, 2009

(65) Prior Publication Data

US 2010/0196397 A1 Aug. 5, 2010

Related U.S. Application Data

(60) Division of application No. 11/151,598, filed on Jun. 13, 2005, now Pat. No. 7,504,224, which is a continuation of application No. 09/738,945, filed on Dec. 15, 2000, now Pat. No. 7,053,179.

(60) Provisional application No. 60/171,042, filed on Dec. 16, 1999, provisional application No. 60/234,572, filed on Sep. 22, 2000.

(51) Int. Cl.
*G01N 33/53* (2006.01)
*C12Q 1/00* (2006.01)
*C07K 1/00* (2006.01)
*A61K 38/00* (2006.01)

(52) U.S. Cl. .................. 435/7.1; 435/4; 435/5; 530/350
(58) Field of Classification Search .................. None
See application file for complete search history.

(56) References Cited

U.S. PATENT DOCUMENTS

| | | | |
|---|---|---|---|
| 5,444,044 | A | 8/1995 | Jiang et al. |
| 5,464,933 | A | 11/1995 | Bolognesi et al. |
| 5,656,480 | A | 8/1997 | Wild et al. |
| 5,780,221 | A | 7/1998 | Schumacher et al. |
| 5,840,843 | A | 11/1998 | Jiang et al. |
| 6,090,911 | A | 7/2000 | Petka et al. |
| 6,150,088 | A | 11/2000 | Chan et al. |
| 6,303,317 | B1 | 10/2001 | Alber et al. |
| 6,372,890 | B1 | 4/2002 | Koshida |
| 6,506,554 | B1 | 1/2003 | Chan et al. |
| 6,747,126 | B1 | 6/2004 | Eckert et al. |
| 6,818,740 | B1 | 11/2004 | Eckert et al. |
| 6,841,657 | B2 | 1/2005 | Eckert et al. |
| 7,053,179 | B2 | 5/2006 | Root et al. |
| 7,226,598 | B2 | 6/2007 | Eckert et al. |
| 7,402,396 | B2 | 7/2008 | Chan et al. |
| 7,504,224 | B2 | 3/2009 | Root et al. |
| 7,811,578 | B2 | 10/2010 | Eckert et al. |
| 2003/0082525 | A1 | 5/2003 | Root et al. |
| 2003/0099935 | A1 | 5/2003 | Chan et al. |
| 2004/0213801 | A1 | 10/2004 | Wild et al. |
| 2005/0221294 | A1 | 10/2005 | Eckert et al. |
| 2008/0269462 | A1 | 10/2008 | Eckert et al. |

FOREIGN PATENT DOCUMENTS

| | | |
|---|---|---|
| WO | WO 94/02505 | 2/1994 |
| WO | WO 96/40191 | 12/1996 |
| WO | WO 98/32848 A | 7/1998 |
| WO | WO 00/06599 | 2/2000 |
| WO | WO 00/40616 | 7/2000 |
| WO | WO 01/03723 A1 | 1/2001 |
| WO | WO 01/44286 A2 | 6/2001 |
| WO | WO 02/24735 A2 | 3/2002 |
| WO | WO 02/24735 A3 | 3/2002 |

OTHER PUBLICATIONS

Desrosiers, RC. "Prospects or an A DS vaccine" NATLRE Medicine;10(3):221-223; 2004.*
Hedestam GB et al. "The challenges of eliciting neutralizing antibodies to HIV-1 and to influenza virus" Nature Reviews. Microbiology; London, Feb. 2008; vol. 6, Iss.2.*
Bahbouhi, B., et al., "Effects of L-and D-REKR Amino Acid-Containing Peptides on HIV and SIV Envelope Glycoprotein Precursor Maturation and HIV and SIV Replication," *Biochem., J.* 366 (Pt. 3):863-872 (2002).
Baum, Rudy, "Virus-cell Fusion Targeted for Drug Development," *C&EN* (1996).
Benkirane, M., et al., "Antigenicicty and Immunogenicity of Modified Synthetic Peptides Containing D-Amino Acid Residues. Antibodies to a D-Enantiomer Do Recognize the Parent L-Hexapeptide and Reciprocally," *J. Biol. Chem.*, 268(35):26279-26285 (1993).
Bernstein, Helene B., et al., "Oligomerization of the Hydrophobic Heptad Repeat of gp41," *J. Virology*, 69(5):2745-2750 (1995).
Blacklow, Stephen C., et al., "A Trimeric Subdomain of the Simian Immunodeficiency Virus Envelope Glycoprotein," *Biochemistry*, 34(46):14955-14962 (1995).
Blake, James and Li, Choh Hao, "Adrenocorticotropin. 47. Synthesis and Biological Activity of Adrenocorticotropic Peptides Modified at the Tryptophan Position," *J. Medicinal Chem.*, 18(4):423-426 (1975). Borchardt, Allen, et al., "Small Molecule-Dependent Genetic Selection In Stochastic Nanodroplets As A Means Of Detecting Protein-Ligand Interactions On A Large Scale," *Chem. & Biol.*, 4(12):961-968 (1997).
Bowie, J.U., et al., "Deciphering the Message in Protein Sequences: Tolerance to Amino Acid Substitutions," *Science*, 247:1306-1310 (1990).
Bullough, Per A., et al., "Structure Of Influenza Haemagglutinin At The Ph Of Membrane Fusion," *Nature*, 371:37-43 (1994).
Butto, et al., "Dual Infection With Different Strains Of The Same HIV-1 subtype," *AIDS*, 11(5):694-696 (1997).
Caffrey, Michael, et al., "Three-Dimensional Solution Structure Of The 44kda Ectodomain Of SIV gp41," *EMBO J.*, 17(16):4572-4584 (1998).
Cao, Jie, et al., "Effects of Amino Acid Changes in the Extracellular Domain of the Human Immunodeficiency Virus Type 1 gp41 Envelope Glycoprotein," *J. Virology*, 67(5):2747-2755 (1993).
Chabala, John C., "Solid-Phase Combinatorial Chemistry And Novel Tagging Methods For Identifying Leads," *Curr.Opin. Biotech.*, 6:632-639 (1995).

(Continued)

*Primary Examiner* — Bo Peng

(74) *Attorney, Agent, or Firm* — Hamilton, Brooks, Smith & Reynolds, P.C.

(57) ABSTRACT

Five-Helix protein, which comprises the three N-helices and at least two, but not three, of the three C-helices of the trimer-of-hairpin structure of HIV gp41, separated by linkers, such as amino acid residue linkers, is disclosed. Six-Helix protein, which includes the three N-helices and the three C-helices of the trimer-of-hairpin structure of HIV gp41, separated by linkers, is also disclosed.

4 Claims, 13 Drawing Sheets

(4 of 13 Drawing Sheet(s) Filed in Color)

OTHER PUBLICATIONS

Chakrabartty, Avijit, et al., "Aromatic Side-Chain Contribution to Far-Ultraviolet Circular Dichroism of Helical Peptides and Its Effect on Measurement of Helix Propensities," *Biochemistry*, 32:5560-5565 (1993).

Chambers, Philip, et al., "Heptad Repeat Sequences are Located Adjacent to Hydrophobic Regions in Several Types of Virus Fusion Glycoproteins," *Journal of General Virology*, 71:3075-3080 (1990).

Chan, David C. and Kim, Peter A., "HIV Entry and Its Inhibition," *Cell*, 93:681-684 (1998).

Chan, David C., et al., "Core Structure of gp41 From the HIV Envelope Glycoprotein," *Cell*, 89:263-273 (1997).

Chan, David C., et al., "Evidence that a Prominent Cavity in the Coiled Coil of HIV Type I gp41 is an Attractive Drug Target," *Proc. Natl. Acad. Sci. USA*, 95:15613-15617 (1998).

Chang, Ding-Kwo, et al., "Proline Affects Oligomerization of a Coiled Coil by Inducing a Kink in a Long Helix," *J. Structural Biology*, 128:270-279 (1999).

Chen, Benjamin K., et al. "Distinct Modes of Human Immunodeficiency Virus Type 1 Proviral Latency Revealed by Superinfection of Nonproductively Infected Cell Lines with Recombinant Luciferase-Encoding Viruses," *J. Virology*, 68(2):654-660 (1994).

Chen, Charlie L., et al., "One Bead-One Compound Combinatorial Peptide Library: Different Types of Screening," *Methods in Enzymology* 267:211-219 (1996).

Chen, Chin-Ho, et al., "A Molecular Clasp in the Human Immunodeficiency Virus (HIV) Type 1 TM Protein Determines the Anti-HIV Activity of gp41 Derivatives:Implication for Viral Fusion," *J. Virology*, 69(6):3771-3777 (1995).

Chen, Steve, et al., "Mutations in the Leucine Zipper-Like Heptad Repeat Sequence of Human Immunodeficiency Virus Type 1 gp41 Dominantly Interfere with Wild-Type Virus Infectivity," *J. of Virology*, 72(6):4795-4774 (1998).

Chen, Yee-Hsiung, et al., "Determination of the Helix and β Form of Proteins in Aqueous Solution by Circular Dichroism," *Biochemistry*, 13(16):3350-3359 (1974).

Cole, James L. and Garsky, Victor M., "Thermodynamics of Peptide Inhibitor Binding to HIV-1 gp41," *Biochemistry*, 40:5633-5641 (2001).

Corigliano-Murphy, M.A., et al., "Synthesis and Properties of an All-D Model Ribonuclease S-Peptide," *Int. J. Pep. Prot. Res.*, 25:225-231 (1985).

Delwart, Eric L., et al., "Retroviral Envelope Glycoproteins Contain a "Leucine Zipper"-like Repeat," *AIDS Research and Human Retroviruses*, 6(6):703-706 (1990).

Doering Don S. and Matsudaira, Paul, "Cysteine Scanning Mutagenesis at 40 of 76 Positions in Villin Headpiece Maps the F-Actin Binding Site and Structural Features of the Domain," *Biochemistry*, 35:12677-12685 (1996).

Dutch, Rebecca Ellis, et al., "Paramyxovirus Fusion Protein: Characterization of the Core Trimer, a Rod-Shaped Complex with Helices in Anti-Parallel Orientation," *Virology*, 254:147-159 (1999), Eckert, D.M., and Kim, P.S., "Design of Potent Inhibitors of HIV-1 Entry from the gp41 N-peptide Region," *PNAS*, 98(20):11187-11192 (2001).

Eckert, Debra M. and Kim, Peter S., "Mechanisms of Viral Membrane Fusion and Its Inhibition," *Annual Rev. Biochem.*,70: 777-810 (2001).

Eckert, Debra M., et al. "Crystal Structure of GCN4-p1$_O$1, a Trimeric Coiled Coil with Buried Polar Residues," *J. Mol. Biol.*, 284:859-865 (1998).

Eckert, Debra M., et a., "Inhibiting HIV-1 Entry: Discovery of D-Peptide Inhibitors that Target the gp41 Coiled-Coil Pocket," *Cell*, 99:103-115 (1999).

Eckhart, Leopold, et al., "Immunogenic Presentation of a Conserved gp41 Epitope of Human Immunodeficiency Virus Type I on Recombinant Surface Antigen of Hepatitis B Virus," *J. Gen. Virol.* 77:2001-2008 (1996).

Edelhoch, Harold, "Spectroscopic Determination of Tryptophan and Tyrosine in Proteins," *Biochemistry*, 6:(7):1948-1954 (1967).

Fahey, et al., "Status of Immune-based Therapies in HIV Infection and AIDS," *Clinical Experimental Immunology*, 888:1-5 (1992).

Fass, Deborah and Kim, Peter S., "Dissection Of A Retrovirus Envelope Protein Reveals Structural Similarity To Influenza Hemagglutinin," *Current Biology*, 5(12): 1-7(1995).

Fass, Deborah et al., "Retrovirus Envelop Domain at 1.7 Resolution," *Nature Structural Biology*, 3(5):465-469 (1996).

Ferrer, Marc, et al., "Selection of gp41-mediated HIV-1 Cell Entry Inhibitors From Biased Combinatorial Libraries Of Non-Natural Binding Elements," *Nature Structural Biology*, 6(10):953-960 (1999).

Furuta, Rika A., et al., "Capture Of An Early Fusion-Active Conformation Of HIV-1 gp41," *Nature Structural Biology*, 5(4):276-279 (1998).

Gallaher, William R., et al., "A General Model for the Transmembrane Proteins of HIV and Other Retroviruses," *Aids Research and Human Retroviruses*, 5(4):431-440 (1989).

Harbury, Pehr B. et al., "Crystal Structure of an Isoleucine-Zipper Trimer," *Nature* 371:80-83 (1994).

Harbury, Pehr B. et al., "Repacking Protein Cores With Backbone Freedom:Structure Prediction For Coiled Coils," *Proc. Natl. Acad. Sci, USA* 92:8408-8412 (1995).

Hirsch, Vanessa M. and Johnson, Philip R., "Pathogenic Diversity of Simian Immunodeficiency Viruses," *Virus Research* 32:183-206 (1994).

Hooft, Rob W.W. and Vriend, Gert, "ERestriction Requirementors in Protein Structures," *Nature* 381:272 (1996).

Jiang, S., et al., "A Screening Assay For Antiviral Compounds Targeted To The HIV-1 Gp41 Core Structure Using A Conformation-Specific Monoclonal Antibody," *J. Virol. Methods*, 80:85-96 (1999).

Jiang, Shibo et al., "A conformation-Specific Monoclonal Antibody Reacting with Fusion-Active gp41 From the Human Immunodeficiency Virus Type 1 Envelope Glycoprotein," J. *of Virology* 72(12):10213-10217 (1998).

Jiang, Shibo, et al., "HIV-1 Inhibition By A Peptide," *Nature*, 365:113 (1993).

Jiang, Shibo, et al., "Development of HIV Entry Inhibitors Targeted to the Coiled-Coil Regions of gp41," *Biochemical and Biophysical Research Communications*, 269(3):641-646 (2000).

Jones, T.A., et al., "Improved Methods for Building Protein Models in Electron Density Maps and the Location of Errors in these Models," *Acta Cryst. A.*, 47:110-119 (1991).

Joyce, J.G., et al., "Enhancement of a-Helicity in the HIV-1 Inhibitory Peptide DP178 Leads to an Increased Affinity for Human Monoclonal Antibody 2F5 But Does Not Elicit Neutralizing Responses in Vitro", *J. Biol. Chem.*, 277(48):45811-45820 (2002).

Judice, J. Kevin, et al., "Inhibition Of HIV Type 1 Infectivity By Constrained A-Helical Peptides: Implications For The Viral Fusion Mechanism," *Proc. Natl. Acad. Sci. USA*, 94:13426-13430 (1997).

Kilby, J. Michael, et al., "Potent Suppression Of HIV-1 Replication In Humans by T-20, a Peptide Inhibitor of gp41-Mediated Virus Entry," *Nature Medicine*, 4(11):1302-1307 (1998).

Kliger, Yossef, et al., "Inhibition of HIV-1 Entry Before gp41 Folds Into its Fusion-active Conformation," *J. Mol. Biol.*, 295:163-168 (2000).

Kliger, Yossef, et al., "Mode of Action of an Antiviral Peptide from HIV-1," *J. Biol. Chem.*, 276(2):1391-1397 (2001).

Kozarsky, Karen, et al., "Glycosylation and Processing of the Human Immunodeficiency Virus Type 1 Envelope Protein," *J. Acquired Immune Deficiency Syndromes*, 2:163-169 (1989).

Kramer, A., et al., "Stepwise Transformation of a Cholera Toxin and a p24 (HIV-1) Epitope Into D-Peptide Analogs," *Prot. Engin.* ,11(10):941-948 (1998).

Kubinyi, Hugo, "Combinatorial and Computational Approaches In Structure-Based Drug Design," *Curr. Op. In Drug Disc. & Dev.* ,1(1):16-22 (1998).

Kuntz, Irwin D., "Structure-Based Strategies for Drug Design and Discovery," *Science*, 257:1078-1082 (Aug. 1992).

LaCasse, Rachel A., et al., "Fusion-Competent Vaccines: Broad Neutralization of Primary Isolates of HIV," *Science*, 283:357-362 (1999).

Lam, Kit S., et al., "A New Type of Synthetic Peptide Library for Identifying Ligand-Binding Activity," *Nature*, 354:82-84 (1991).

Lambert, D.M., et al., "Peptides From Conserved Regions Of Paramyxovirus Fusion (F) Proteins Are Potent Inhibitors Of Viral Fusion," *Proc. Natl. Acad. Sci. USA*, 93:2186-2191 (1996).

Letvin, Norman L., "Progress in the Development of an HIV-1 Vaccine," *Science*, 280:1875-1880 (1998).

Levy, R.B., et al., "T Lymphocytes Can Recognize Determinants Unique to Neuropeptides of Guinea Pig Myelin Basic Protein Containing a Single D-Isomer Amino Acid Substitution," *J. Neuro. Res.*, 25(1):29-38 (1990).

Li, Zhe, et al., "Anti-malarial Drug Development Using Models of Enzyme Structure," *Chemistry & Biology*, 1:31-37 (1994).

Lu, Min and Kim, Peter S., "A Trimeric Structural Subdomain of the HIV-1 Transmembrane Glycoprotein," *J. Biomol. Structure & Dynamics*, 15(3):465-471 (1997).

Lu, Min, et al., "A Trimeric Structural Domain of the HIV-1 Transmembrane Glycoprotein," *Nature Structural Biology*, 2(12):1-8 (1995).

Malashkevich, Vladimir N., et al., "Core Structure of the Envelope Glycoprotein GP2 From Ebola Virus at 1.9- Resolution," *Proc. Natl. Acad. Sci. USA*, 96:2662-2667 (1999).

Malashkevich, Vladimir N., et al., "Crystal Structure Of The Simian Immunodeficiency Virus (SIV) gp41 Core: Conserved Helical Interactions Underlie The Broad Inhibitory Activity of gp41 Peptides," *Proc. Natl. Acad. Sci. USA*, 95:9134-9139 (1998).

Manchester, M., et al., "Identification Of Temperature-Sensitive Mutants Of The Human Immunodeficiency Virus Type 1 Protease Through Saturation Mutagenesis," *J. Biol. Chem.*, 269(10):7689-7695 (1994).

Meng, Elaine C., et al., "Automated Docking With Grid-Based Energy Evaluation," *Journal of Computational Chemistry*, 13(4):505-524 (1992).

Miller, M.D. and Geleziunas, R., "A Human Monoclonal Antibody Blocks HIV Entry by a T20-Like Mechanism", Abstract presented at the 13th International HIV Drug Resistance Workshop, Jul. 8-12, 2004, Tenerife, Canary Islands, Spain.

Miller, M.D., et al., "A Human Monoclonal Antibody Neutralizes Diverse HIV-1 Isolates by Binding a Critical gp41 Epitope," *PNAS* 102(41):14759-14764 (2005).

Moschella, F., et al.. "Administration of Different Antigenic Forms of Altered Peptide Ligands Derived From HIV-1 R Tase Influence Their Effects on T Helper Cell Activation," *Hum. Immunol.*, 64:1-8 (2003).

Muster, Thomas, et al., "A Conserved Neutralizing Epitope on gp41 of Human Immunodeficiency Virus Type 1," *J. Virology*, 67(11):6642-6647 (1993).

Muster, Thomas, et al., "Cross-Neutralizing Activity against Divergent Human Immunodeficiency Virus Type 1 Isolates Induced by the gp41 Sequence ELDKWAS," *J. Virology*, 68(6):4031-4034 (1994).

Nautiyal, Shivani and Alber, Tom, "Crystal Structure of a Designed, Thermostable, Heterotrimeric Coiled Coil," *Protein Science*, 8:84-90 (1999).

Nolte, Alexis, et al., "Mirror-design of L-Oligonucleotide Ligands Binding to L-arginine," *Nature Biotechnology*, 4:1116-1119 (1996).

O'Neil, Karyn T. and DeGrado, William F., "A Thermodynamic Scale for the Helix-Forming Tendencies of the Commonly Occurring Amino Acids," *Science*, 250:646-351 (1990).

Poumbourios, Pantelis, et al., "Human Immunodeficiency Virus Type 1 Envelope Glycoprotein Oligomerization Requires the gp41 Amphipathic α-Helical/Leucine Zipper-Like Sequence," *J. Virology*, 71(3):2041-2049 (1997).

Purtscher, Martin, et al., "Restricted Antigenic Variability of the Epitope Recognized by the Neutralizing gp41 Antibody 2F5," *AIDS*, 10:587-593 (1996).

Reimann, Keith A., et al., "A Chimeric Simian/Human Immunodeficiency Virus Expressing a Primary Patient Human Immunodeficiency Virus Type 1 Isolate env Causes an AIDS-Like Disease after In Vivo Passage in Rhesus Monkeys," *J. Virology*, 70(10):6922-6928 (1996).

Richman, Douglas D., "Nailing down another HIV target," *Nature Medicine*, 4(11):1232-1233 (1998).

Richman, et al., "Rapid Evolution of the Neutralizing Antibody Response to HIV Type 1 Infection," *Proceeding of the National Academy of Science*, 100(7):4144-4149 (2003).

Rimsky, Laurence T., et al., "Determinants of Human Immunodeficiency Virus Type 1 Resistance to gp41-Derived Inhibitory Peptides," *J. Virology*, 72(2):986-993 (1998).

Ring, Christine S., et al., "Structure-based Inhibitor Design by Using Protein Models for the Development of Antiparasitic Agents," *Proc. Natl. Acad. Sci. USA*, 90:3583-3587 (1993).

Root, Michael J., et al., "Protein Design of an HIV-1 Entry Inhibitor," *Science*, 291:884-888 (2001).

Rudinger, J., "Characteristics of the Amino Acids as Components of a Peptide Hormone Sequence" In *Peptide Hormones*, J.A. Parsons, ed. (Baltimore: University Park Press), pp. 1-6 (1976).

Schumacher, Ton N.M., et al., "Identification of D-Peptide Ligands Through Mirror-Image Phage Display," *Science*, 271:1854-1857 (1996).

Shuker, Suzanne B., et al., "Discovering High-Affinity Ligands for Proteins: SAR by NMR," *Science*, 274:1531-1534 (1996).

Singh, Mona, et al., "LearnCoil-VMF: Computational Evidence for Coiled-coil-like Motifs in Many Viral Membrane-fusion Proteins," *J. Mol. Biol.* 290:1031-1041 (1999).

Suzuki, K., et al., "An Isoleucine Zipper Peptide Forms a Native-like Triple Stranded Coiled Coil in Solution," *Protein Engineering* 11(11):1051-1055 (1998).

Tan, Kemin, et al., "Atomic Structure of a Thermostable Subdomain of HIV-1 gp41," *Proc. Natl. Acad. Sci. USA*, 94:12303-12308 (1997).

Tarrago-Litvak, Laura, et al., "The Reverse Transcriptase of HIV-1: From Enzymology to Therapeutic Intervention," *FASEB J.*, 8:497-503 (1994).

Tucker, Thomas J., et al. "Development of Nonnucleoside HIV Reverse Transcriptase Inhibitors," *Methods in Enzymology*, 275:440-472 (1996).

Tyagi, Sanjay, et al., "Multicolor Molecular Beacons for Allele Discrimination," *Nature Biotechnology*, 16:49-53 (1998).

Weissenhorn, W., et al., "Atomic Structure of the Ectodomain From HIV-1 gp41," *Nature*, 387:426-430 (1997).

Weissenhorn, Winfried, et al., "Assembly of a Rod-Shaped Chimera Of A Trimeric GCN4 Zipper and the HIV-1 gp41 ectodomain Expressed in *Escherichia coli*," *Proc. Natl. Acad. Sci. USA*, 94:6065-6069 (1997).

Weissenhorn, Winfried, et al., "Crystal Structure of the Ebola Virus Membrane Fusion Subunit, GP2, from the Envelope Glycoprotein Ectodomain," *Molecular Cell*, 2:605-616 (1998).

Weng, Y., et al., "Mutational Analysis of Residues in the Coiled-Coil Domain of Human Immunodeficiency Virus Type 1 Transmembrane Protein gp41," *J. Virol.* 72(12):9676-9682 (1998).

Wild, Carl, et al.. "A Synthetic Peptide Inhibitor of Human Immunodeficiency Virus Replication: Correlation Between Solution Structure and Viral Inhibition," *Proc. Natl. Acad. Sci. USA*, 89:10537-10541 (1992).

Wild, Carl T. et al., "Peptides Corresponding To A Predictive Alpha-Helical Domain Of Human Immunodeficiency Virus Type 1 gp41 Are Potent Inhibitors Of Virus Infection," *Proc. Natl. Acad. Sci. USA*, 91:9770-9774 (1994).

Williams, Kelly P., et al., "Bioactive And Nuclease-Resistant L-DNA Ligand Of Vasopressin," *Proc. Natl. Acad. Sci. USA*, 94:11285-11290 (1997).

Yang, Xinzhen, et al., "Characterization of Stable, Soluble Trimers Containing Complete Ectodomains of Human Immunodeficiency Virus Type 1 Envelope Glycoproteins," *J. Virol.* 74(12):5716-5725 (2000).

Youngquist, R. Scott, et al., "Generation and Screening of Combinatorial Peptide Libraries Designed for Rapid Sequencing by Mass Spectrometry," *J. Am. Chem. Soc.*, 117:3900-3906 (1995).

Notification of Transmittal of the International Preliminary Examination Report (IPER) with IPER, PCT/U599/17351, mailed Oct. 31, 2000.

Notification of Transmittal of the International Search Report (ISR) or the Declaration with ISR, PCT/U599/17351, mailed Jan. 18, 2000.

Written Opinion, PCT/US99/17351, mailed Apr. 5, 2000.

Office Action, Canada 2,338,022, dated Jan. 3, 2007.

Reply, Canada 2,338,022, dated Jul. 3, 2007.

Supplemental Reply, Canada 2,338,022, dated Aug. 3, 2007.

Office Action, Canada 2,338,022, dated Jan. 2, 2008.

Reply, Canada 2,338,022, dated Jul. 2, 2008.

Office Action, Canada 2,338,022, dated Jul. 2, 2008.

Reply, Canada 2,338,022, filed Jan. 4, 2010.

Office Action, EP 99937691.6, dated Mar. 21, 2006.

Reply, EP 99937691.6, mailed Aug. 30, 2006.
Office Action, EP 99937691.6, dated Feb. 6, 2008.
Reply, EP 99937691.6, mailed Jun. 6, 2008.
Office Action, EP 99937691.6, dated Jun. 18, 2009.
Reply, EP 99937691.6, dated Dec. 8, 2009.
Office Action, JP 2000-562395, dated Sep. 3, 2009.
Reply to Request for Examination, Australia 57886/01, dated Apr. 10, 2002.
Reply, Australia 57886/01, mailed Nov. 25, 2003.
Office Action, Australia 57886/01, dated Dec. 24, 2003.
Reply, Australia 57886/01, mailed Jan. 5, 2004.
Office Action, 10-2001-7001273, dated Dec. 19, 2005.
Notification of Transmittal of the International Preliminary Examination Report (IPER) with IPER, PCT/US01/29637, mailed Feb. 17, 2003.
Notification of Transmittal of the International Search Report (ISR) or the Declaration with ISR, PCT/US01/29637, mailed Jan. 22, 2003.
Office Action, Australia 2001292944 dated Apr. 21, 2004.
Reply, Australia 2001292944 dated Jul. 5, 2005.
Office Action, EP 01973355.9 dated May 26, 2006.
Reply, EP 01973355.9 mailed Dec. 4, 2006.
Office Action, EP 01973355.9 dated Sep. 21, 2007.
Reply, EP 01973355.9 mailed Jan. 24, 2008.
Office Action, EP 01973355.9 dated Aug. 12, 2008.
Reply, EP 01973355.9 mailed Feb. 6, 2009.
Office Action, EP 01973355.9 dated May 5, 2009.
Reply, EP 01973355.9 mailed May 20, 2009.
Official Action, Australia 2005225063, dated Sep. 20, 2007.
Reply, Australia 2005225063, dated May 7, 2009.
Further Official Action, Australia 2005225063, mailed May 15, 2009.
Reply, Australia 2005225063, dated May 25, 2009.
Notification of Transmittal of the International Preliminary Examination Report (IPER) with IPER, PCT/US00/34194, mailed Apr. 11, 2002.
International Search Report, PCT/US00/34194, mailed Jul. 10, 2001.
Written Opinion, PCT/US00/34194, mailed Dec. 14, 2001.
Requisition by the Examiner, 2,395,291 Canada, mailed Feb. 4, 2008.
Response to Requisition, 2,395,291 Canada, filed Aug. 1, 2008.
Office Action, 2,395,291 Canada, dated Jul. 24, 2009.
Office Action, EP 00986475.2, dated Aug. 22, 2003.
Reply to Office Action, EP 00986475.2, mailed Feb. 27, 2004.
Office Action, EP 00986475.2, dated Dec. 3, 2004.
Reply to Office Action, EP 00986475.2, mailed Jun. 7, 2005.
Office Action, EP 00986475.2, dated Jun. 30, 2006.
Reply to Office Action, EP 00986475.2, mailed Oct. 19, 2006.
Communication under Rule 51(4) EPC, EP 00986475.2, mailed May 22, 2007.
Reply to Communication, EP 00986475.2, mailed Sep. 5, 2007.
Preliminary Amendment, U.S. Appl. No. 11/976,764, filed Mar. 11, 2009.
Office Action, U.S. Appl. No. 11/976,764, dated Apr. 3, 2009.
Reply, U.S. Appl. No. 11/976,764, filed Jun. 30, 2009.
Office Action, U.S. Appl. No. 11/976,764, dated Nov. 5, 2009.
Office Action (Restriction Requirement), dated Mar. 22, 2007, U.S. Appl. No. 10/987,687.
Reply, U.S. Appl. No. 10/987,687, filed Jun. 14, 2007.
Office Action, U.S. Appl. No. 10/987,687, dated Sep. 4, 2007.
Reply, U.S. Appl. No. 10/987,687, filed Dec. 4, 2007.
Office Action, U.S. Appl. No. 10/987,687 dated Mar. 7, 2008.
Reply, U.S. Appl. No. 10/987,687, filed May 19, 2008.
Office Action, U.S. Appl. No. 10/987,687 dated Sep. 17, 2008.
Reply, U.S. Appl. No. 10/987,687, filed Mar. 16, 2009.
Office Action, U.S. Appl. No. 10/987,687 dated Jul. 6, 2009.
Office Action (Restriction Requirement), U.S. Appl. No. 09/746,742 dated Sep. 24, 2002.
Reply to Restriction Requirement, U.S. Appl. No. 09/746,742, filed Mar. 24, 2003.
Supplemental Restriction Requirement, U.S. Appl. No. 09/746,742 dated Jun. 6, 2003.
Reply to Supplemental Restriction Requirement, U.S. Appl. No. 09/746,742, filed Aug. 29, 2003.
Office Action, Bonafide Attempt Letter, U.S. Appl. No. 09/746,742 dated Nov. 17, 2003.
Reply, U.S. Appl. No. 09/746,742, filed Dec. 11, 2003.
Office Action, U.S. Appl. No. 09/746,742 dated Mar. 10, 2004.
Reply, U.S. Appl. No. 09/746,742, filed Jul. 12, 2004.
Notice of Allowance, U.S. Appl. No. 09/746,742 dated Aug. 24, 2004.
Office Action (Restriction Requirement), U.S. Appl. No. 09/668,072 dated Aug. 21, 2002.
Reply, U.S. Appl. No. 09/668,072, filed Dec. 19, 2002.
Office Action, U.S. Appl. No. 09/668,072 dated Mar. 19, 2003.
Reply, U.S. Appl. No. 09/668,072, filed Sep. 19, 2003.
Notice of Allowance, U.S. Appl. No. 09/668,072 dated Dec. 2, 2003.
Office Action, U.S. Appl. No. 10/395,817 dated Jun. 30, 2006.
Reply, U.S. Appl. No. 10/395,817, filed Sep. 29, 2006.
Notice of Allowance, U.S. Appl. No. 10/395,817 dated Jan. 12, 2007.
Notice to File Corrected Application Papers, U.S. Appl. No. 10/395,817 dated Feb. 13, 2007.
Replacement Drawings, U.S. Appl. No. 10/395,817, filed Mar. 15, 2007.
Communication from Examiner dated Apr. 16, 2007, U.S. Appl. No. 10/395,817.
Office Action (Restriction Requirement), U.S. Appl. No. 09/364,497 dated May 17, 2001.
Reply, U.S. Appl. No. 09/364,497, filed Jun. 18, 2001.
Office Action, U.S. Appl. No. 09/364,497 dated Sep. 11, 2001.
Reply, U.S. Appl. No. 09/364,497, filed Feb. 11, 2002.
Office Action (2nd Restriction Requirement), U.S. Appl. No. 09/364,497 dated May 22, 2002.
Reply, U.S. Appl. No. 09/364,497, filed Sep. 23, 2002.
Office Action, U.S. Appl. No. 09/364,497 dated Mar. 12, 2003.
Reply, U.S. Appl. No. 09/364,497, filed Sep. 12, 2003.
Office Action, U.S. Appl. No. 09/364,497 dated Jan. 14, 2004.
Interview Summary, U.S. Appl. No. 09/364,497 dated Mar. 4, 2004.
Amendment After Final, U.S. Appl. No. 09/364,497, filed Mar. 12, 2004.
Advisory Action, U.S. Appl. No. 09/364,497 dated Jun. 2, 2004.
Notice of Allowance, U.S. Appl. No. 09/364,497 dated Jun. 29, 2004.
Office Action (Restriction Requirement), U.S. Appl. No. 09/738,945, dated Jun. 3, 2003.
Reply, U.S. Appl. No. 09/738,945, filed Sep. 2, 2003.
Office Action, U.S. Appl. No. 09/738,945 dated Nov. 17, 2003.
Reply, U.S. Appl. No. 09/738,945, filed May 17, 2004.
Office Action, U.S. Appl. No. 09/738,945 dated Sep. 22, 2004.
Reply, U.S. Appl. No. 09/738,945, filed Feb. 22, 2005.
Notice of Allowance, U.S. Appl. No. 09/738,945 dated Apr. 11, 2005.
Office Action (RR), dated Sep. 24, 2003, U.S. Appl. No. 10/173,570.
Reply dated Oct. 24, 2003, U.S. Appl. No. 10/173,570.
Office Action, dated Jan. 28, 2004, U.S. Appl. No. 10/173,570.
Reply, dated Jul. 26, 2004, U.S. Appl. No. 10/173,570.
Office Action, dated Dec. 20, 2004, U.S. Appl. No. 10/173,570.
Notice of Appeal, dated Mar. 16, 2005, U.S. Appl. No. 10/173,570.
Office Action (Restriction Requirement), U.S. Appl. No. 11/151,598 dated Jun. 4, 2007.
Reply, U.S. Appl. No. 11/151,598, filed Jul. 5, 2007.
Office Action, U.S. Appl. No. 11/151,598 dated Sep. 13, 2007.
Reply, U.S. Appl. No. 11/151,598, filed Mar. 12, 2008.
Office Action, U.S. Appl. No. 11/151,598 dated May 30, 2008.
Reply, U.S. Appl. No. 11/151,598, filed Sep. 2, 2008.
Notice of allowance, U.S. Appl. No. 11/151,598 dated Oct. 20, 2008.
Office Action (Restriction Requirement), U.S. Appl. No. 09/062,241, dated Dec. 4, 1998.
Reply, U.S. Appl. No. 09/062,241, filed Apr. 22, 1999.
Office Action, U.S. Appl. No. 09/062,241, dated Jul. 15, 1999.
Reply, U.S. Appl. No. 09/062,241, filed Jan. 17, 2000.
Office Action, U.S. Appl. No. 09/062,241 dated Mar. 3, 2000.
Reply, U.S. Appl. No. 09/062,241, filed May 3, 2000.
Notice of Allowance, U.S. Appl. No. 09/062,241 dated May 22, 2000.
Office Action (Restriction Requirement), U.S. Appl. No. 09/484,925, dated Mar. 27, 2001.
Reply, U.S. Appl. No. 09/484,925, filed Aug. 27, 2001.
Office Action, U.S. Appl. No. 09/484,925, dated Nov. 8, 2001.
Reply, U.S. Appl. No. 09/484,925, filed Feb. 8, 2002.
Notice of Allowance, U.S. Appl. No. 09/484,925 dated Apr. 22, 2002.
Office Action (RR), dated Apr. 8, 2003, U.S. Appl. No. 10/200,007.

Office Action (Restriction Requirement), U.S. Appl. No. 10/680,853, dated Sep. 25, 2006.
Reply, U.S. Appl. No. 10/680,853, filed Nov. 27, 2006.
Office Action, U.S. Appl. No. 10/680,853 dated Feb. 21, 2007.
Reply, U.S. Appl. No. 10/680,853, filed Aug. 20, 2007.
Notice of Allowance, U.S. Appl. No. 10/680,853 dated Feb. 22, 2008.
Office Action, Canada 2,423,004 dated Dec. 10, 2009.
Supplemental Reply, EP 99937691.6, dated Mar. 1, 2010.
Rabenstein, M. and Shi, Y.K., "A Peptide From the Heptad Repeat of Human Immunodeficiency Virus gp41 Shows Both Membrane Binding and Coiled-Coil Formation," *Biochemistry* 34:13390-13397 (1995).
Reply, U.S. Appl. No. 10/978,687, filed Dec. 3, 2009.
Office Action, U.S. Appl. No. 10/978,687, dated Feb. 23, 2010.
Lupas, A., "Coiled Coils: New Structures and New Functions," TIBS 21:375-382 (1996).
Muller, K.M., et al., "Protein Fusions to Coiled-coil Domains," in Methods in Enzymology 328, Thorner, J., et al., eds., (Academic Press USA), pp. 261-282 (2000).
Supplemental Reply, Canada 2,338,022, filed Apr. 19, 2010.
Office Action, JP 2000-562395, dated Apr. 13, 2010.
Reply, Canada 2,423,004, filed Jun. 10, 2010.
Reply, Canada 2,395,291, filed Jan. 21, 2010.
Office Action, JP 2001-544774, dispatched: Aug. 3, 2010.
Reply, U.S. Appl. No. 10/987,687, filed Aug. 23, 2010*.
Final Office Action, U.S. Appl. No. 10/987,687, dated Nov. 3, 2010*.
Office Action, Canada 99937691.6, dated Feb. 18, 2011.
Office Action, Japan 2000-562395, dated Jan. 25, 2011.
Office Action, Canada 2,423,004 dated Feb. 1, 2011.
Office Action, Canada 2,395,291, dated Dec. 15, 2010.
Reply, U.S. Appl. No. 10/987,687, filed Dec. 23, 2010*.
Notice of Allowance, U.S. Appl. No. 10/987,687, dated Feb. 23, 2011*.
Office Action, Japan 2002-529143, dated Feb. 28, 2011.

* cited by examiner

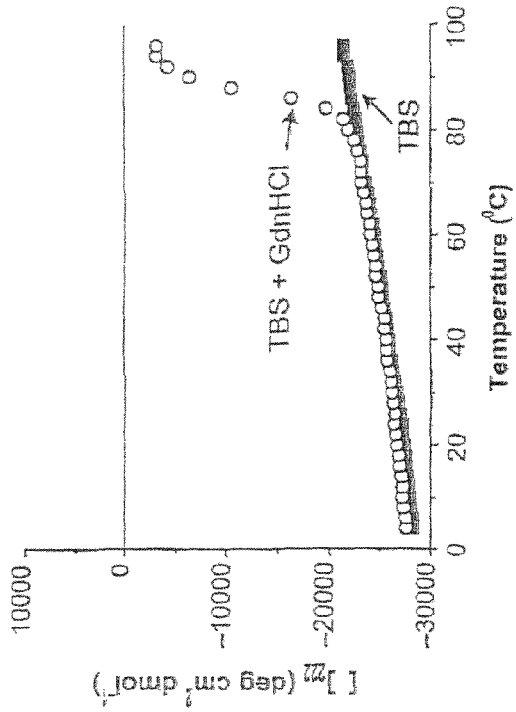
Figure 2B
Figure 2A
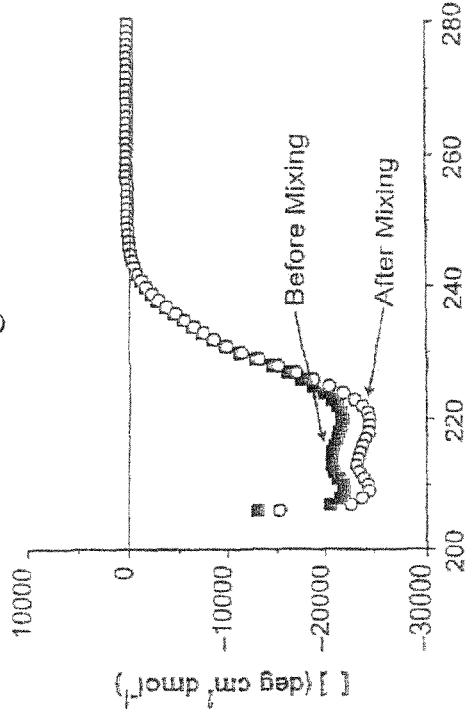
Figure 2D
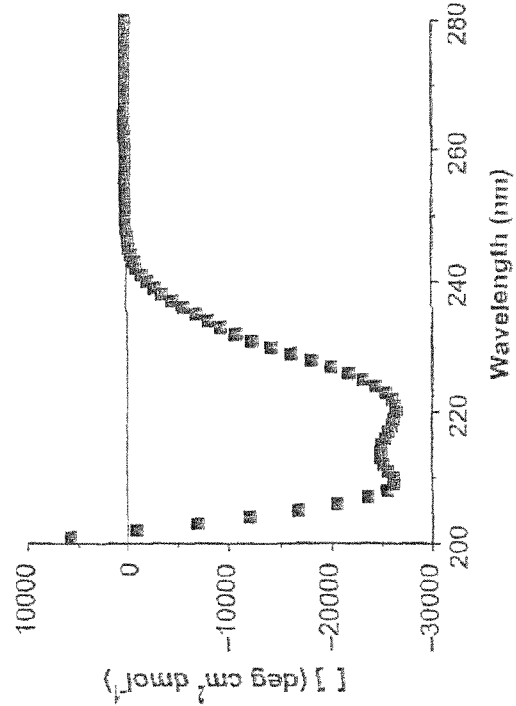
Figure 2C

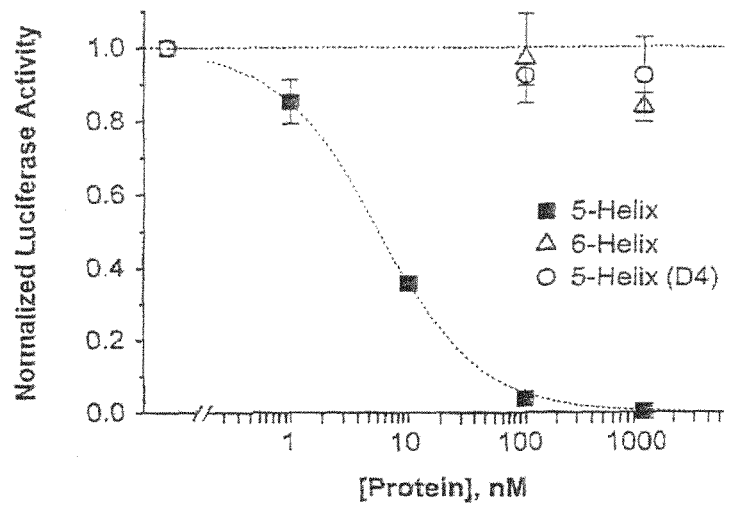
Figure 3A
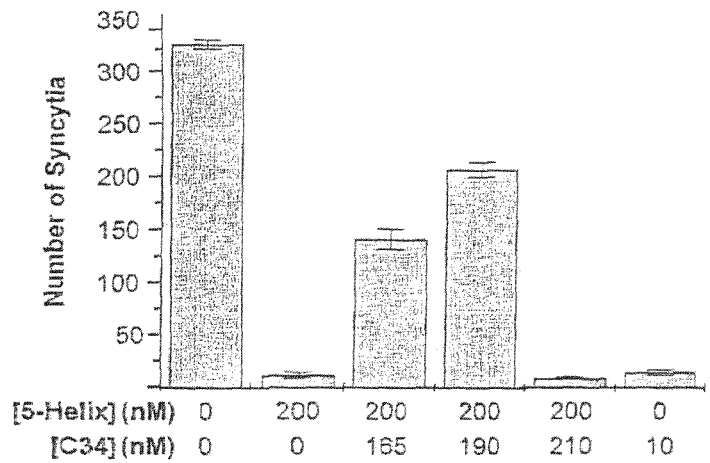
Figure 3B
Figure 3C
| Isolate | Clade | Coreceptor | $IC_{50}$ (nM) |
|---|---|---|---|
| HXB2 | B | CXCR4 | 1.9 ± 0.7 |
| UG024.2 | D | CXCR4 | 1.3 ± 0.2 |
| JRFL | B | CCR5 | 5.6 ± 0.7 |
| RW020.5 | A | CCR5 | 5.9 ± 2.7 |

6-Helix (SEQ ID NO: 2)

5-Helix (SEQ ID NO: 1)

a) View from top of molecule     b) Side view

Sequence overview for 5-Helix paper:

(N40) = QLLSGIVQQQNNLLRAIEAQQHLLQLTVWGIKQLQARILA (SEQ. ID No.: 3)

(C38) = HTTWMEWDREINNYTSLIHSLIEESQNQQEKNEQELLE (SEQ ID No.: 4)

(C37-H6) = GGHTTWMEWDREINNYTSLIHSLIEESQNQQEKNEQELLGGHHHHHH (SEQ ID No.: 5)

(N40**) = QLLSGIDQQQNNLDRAIEAQDHLLQLTDWGIKQLQARILA (SEQ ID No.: 6)

---

6-Helix

SEQ ID No.: 2

M-(N40)-GGSGG-(C38)-GSSGG-(N40)-GGSGG-(C38)-GSSGG-(N40)-GGR-(C37-H6)

MQLLSGIVQQQNNLLRAIEAQQHLLQLTVWGIKQLQARILAGGSGGHTTWMEW
DREINNYTSLIHSLIEESQNQQEKNEQELLEGSSGGQLLSGIVQQQNNLLRAIEA
QQHLLQLTVWGIKQLQARILAGGSGGHTTWMEWDREINNYTSLIHSLIEESQNQ
QEKNEQELLEGSSGGQLLSGIVQQQNNLLRAIEAQQHLLQLTVWGIKQLQARIL
AGGRGGHTTWMEWDREINNYTSLIHSLIEESQNQQEKNEQELLGGHHHHHH

---

5-Helix-R Untagged

SEQ ID No.: 1

M-(N40)-GGSGG-(C38)-GSSGG-(N40)-GGSGG-(C38)-GSSGG-(N40)-GGR

MQLLSGIVQQQNNLLRAIEAQQHLLQLTVWGIKQLQARILAGGSGGHTTWMEW
DREINNYTSLIHSLIEESQNQQEKNEQELLEGSSGGQLLSGIVQQQNNLLRAIEA
QQHLLQLTVWGIKQLQARILAGGSGGHTTWMEWDREINNYTSLIHSLIEESQNQ
QEKNEQELLEGSSGGQLLSGIVQQQNNLLRAIEAQQHLLQLTVWGIKQLQARIL
AGGR

Figure 11A

His-tagged 5-Helix

SEQ ID No.: 7

M-(N40)-GGSGG-(C38)-GSSGG-(N40)-GGSGG-(C38)-GSSGG-(N40)-GG(H)$_6$

MQLLSGIVQQQNNLLRAIEAQQHLLQLTVWGIKQLQARILAGGSGGHTTWMEW
DREINNYTSLIHSLIEESQNQQEKNEQELLEGSSGGQLLSGIVQQQNNLLRAIEA
QQHLLQLTVWGIKQLQARILAGGSGGHTTWMEWDREINNYTSLIHSLIEESQNQ
QEKNEQELLEGSSGGQLLSGIVQQQNNLLRAIEAQQHLLQLTVWGIKQLQARIL
AGGHHHHHH

---

5-Helix (D4)

SEQ ID No.: 8

M-(N40)-GGSGG-(C38)-GSSGG-(N40)-GGSGG-(C38)-GSSGG-**(N40\*\*)**-GG(H)$_6$

MQLLSGIVQQQNNLLRAIEAQQHLLQLTVWGIKQLQARILAGGSGGHTTWMEW
DREINNYTSLIHSLIEESQNQQEKNEQELLEGSSGGQLLSGIVQQQNNLLRAIEA
QQHLLQLTVWGIKQLQARILAGGSGGHTTWMEWDREINNYTSLIHSLIEESQNQ
QEKNEQELLEGSSGGQLLSGIDQQQNNLDRAIEAQDHLLQLTDWGIKQLQARIL
AGGHHHHHH

---

5-Helix-H6-GC

SEQ ID No.: 9

M-(N40)-GGSGG-(C38)-GSSGG-(N40)-GGSGG-(C38)-GSSGG-(N40)-GG(H)$_6$-GC

MQLLSGIVQQQNNLLRAIEAQQHLLQLTVWGIKQLQARILAGGSGGHTTWMEW
DREINNYTSLIHSLIEESQNQQEKNEQELLEGSSGGQLLSGIVQQQNNLLRAIEA
QQHLLQLTVWGIKQLQARILAGGSGGHTTWMEWDREINNYTSLIHSLIEESQNQ
QEKNEQELLEGSSGGQLLSGIVQQQNNLLRAIEAQQHLLQLTVWGIKQLQARIL
AGGHHHHHHGC

Figure 11B

C-peptides

C34

SEQ ID No.: 10

WMEWDREINNYTSLIHSLIEESQNQQEKNEQELL

---

C37-H6

SEQ ID No.: 5

GGHTTWMEWDREINNYTSLIHSLIEESQNQQEKNEQELLGGHHHHHH

Figure 11C

FIVE-HELIX PROTEIN

RELATED APPLICATION(S)

This application is a divisional of U.S. application Ser. No. 11/151,598 filed Jun. 13, 2005, which issued as U.S. Pat. No. 7,504,224, which is a continuation of U.S. application Ser. No. 09/738,945, filed Dec. 15, 2000, which issued as U.S. Pat. No. 7,053,179 and which claims the benefit of U.S. Provisional Application No. 60/171,042, filed Dec. 16, 1999 and U.S. Provisional Application No. 60/234,572, filed Sep. 22, 2000. The entire teachings of the above applications are incorporated herein by reference.

GOVERNMENT SUPPORT

The invention was supported, in whole or in part, by Grant Number PO1 GM 56552 from National Institutes of Health. The Government has certain rights in the invention.

BACKGROUND OF THE INVENTION

HIV is the virus that is responsible for the worldwide AIDS epidemic. The initial stages of HIV infection involve the fusion of the viral membrane with the target cell membrane, a process that injects the viral contents into the cellular cytoplasm. On the viral side, the molecular complex responsible for the fusion activity contains the surface protein gp120 and the transmembrane protein gp41. It is currently believed that gp120 interacts with the proteins CD4 and coreceptors on the target cell, resulting in a conformational change that causes gp41 to insert its amino terminus (fusion peptide region) into the target cell membrane. This structural rearrangement promotes the fusion of virus and cellular membranes through a poorly understood mechanism.

SUMMARY OF THE INVENTION

The present invention relates to a novel protein, referred to as Five (5)-Helix or Five-Helix protein, that, under the conditions described herein, folds into a stable structure, binds a peptide (referred to as C34) that corresponds to the C-peptide region of HIV gp41 or a portion of the region, and inhibits HIV infection of mammalian cells, such as human cells. Five-Helix is made up of the three N-helices and at least two, but not three, of the three C-helices of the trimer of hairpin structure of HIV gp41, separated by linkers, such as amino acid residue linkers. That is, Five-Helix includes the three N-helices and at least two of the three C-helices of HIV gp41. It can also include a portion of the third C-helix, but does not include the entire third C-helix. In each case, the helices are separated by linkers, preferably amino acid residue linkers, between the preceding and following helices. In one embodiment, Five-Helix can be represented as: N-linker-C-linker-N-linker-C-linker-N, wherein N represents an N-helix and C represents a C-helix or C-helix portion. As used herein, the term Five-Helix or Five-Helix protein encompasses all such embodiments (those including three N-helices and two or more, but less than three complete C-helices, separated by appropriate linkers). The amino acid composition of Five-Helix can vary greatly, provided that Five-Helix presents a surface that is structurally complementary to the C-peptide region of HIV gp41 protein and, preferably, binds C34 or the C-peptide region of gp41, as peptides or part of gp41 as a whole. That is, the remaining (interacting) surface of Five-Helix (the C-peptide binding site, all or a portion of which is not occupied by a C-peptide) must be presented in such a manner (conformation) that it is available to bind the C-peptide region of HIV gp41. In the case of vaccine and therapeutic applications of Five-Helix, Five-Helix must bind (be capable of binding) C34 or the C-peptide region of HIV gp41. In the cases in which Five-Helix is used as a drug-screening tool or an antibody-screening tool, Five-Helix need not bind (need not be capable of binding) C34 or the C peptide region of HIV gp41.

In one embodiment, Five-Helix has the amino acid sequence of SEQ ID NO.: 1. In other embodiments, Five-Helix presents a surface that is structurally complementary to the C-peptide region, preferably binds C34 or the C-peptide region and has an amino acid sequence that differs from that of SEQ ID NO.: 1 by addition, deletion, substitution or alteration of at least one amino acid residue. The order of the N-helices and C-helices of Five-Helix can also vary, provided that the conformation is such that the exposed protein presents a surface structurally complementary to the C-peptide region of HIV gp41. The linkers can be of any length or composition, provided that the Five-Helix protein conformation, described above, is retained. Five-Helix can be an L-amino acid protein, a D-amino acid protein or a combination of L-amino acid residues and D-amino acid residues; these residues can be modified residues.

The present invention further relates to DNA encoding Five-Helix; methods of producing Five-Helix; methods in which Five-Helix is used, such as in methods of inhibiting entry of HIV into mammalian cells, including human cells, and methods of eliciting an immune response in an individual, such as a human; methods in which DNA encoding Five-Helix is used, such as in gene therapy methods; genetically engineered cells, such as bacteria, human and other mammalian and other eukaryotic cells, which contain and express Five-Helix protein-encoding DNA and methods of using such cells (e.g., for gene therapy or Five-Helix production); compositions, such as pharmaceutical compositions, which include Five-Helix; Five-Helix complex comprising Five-Helix and a component that binds HIV envelope protein (e.g., gp120); compositions, such as pharmaceutical compositions, which include Five-Helix complex; antibodies, particularly neutralizing antibodies which bind Five-Helix and methods in which such antibodies are used, such as methods of reducing HIV infection; and methods of identifying molecules or compounds that inhibit HIV infection of cells and/or bind the Five-Helix protein.

Five-Helix is useful as an anti-HIV therapeutic agent, a prophylactic agent or drug to prevent HIV infection, a reagent for identifying (screening for) or designing other anti-HIV therapeutics or prophylactics, and an immunogen to elicit antibodies that prevent or reduce HIV infection. In a specific embodiment, the invention relates to a method of identifying a compound or molecule that binds Five-Helix and inhibits HIV infection of mammalian cells, wherein the compound or molecule to be assessed is referred to as a candidate inhibitor, comprising combining a candidate inhibitor and Five-Helix, under conditions appropriate for binding of an inhibitor and Five-Helix to occur and determining if binding occurs, wherein if binding occurs, the candidate inhibitor is a compound or molecule that binds Five-Helix. The method optionally further comprises determining if the compound or molecule that binds Five-Helix inhibits HIV infection of mammalian (e.g., human) cells, such as in a cell-based assay. Such a compound or molecule will inhibit (totally or partially) HIV infection of cells (e.g., by preventing or interfering with formation of the trimer-of-hairpins).

In another embodiment, the invention relates to a method of eliciting an immune response to HIV in an individual, comprising introducing, by an appropriate route, a composition comprising Five-Helix and a physiologically acceptable carrier, in a dose sufficient to elicit the immune response in the individual. Vaccines comprising Five-Helix (or a variant or portion thereof) in a physiologically acceptable carrier are the subject of this invention.

Also the subject of the present invention is Six (6)-Helix protein, which comprises three N-helices and three C-helices of HIV gp41, joined by linkers, such as amino acid residue linkers. In one embodiment, Six-Helix protein comprises the amino acid sequence of SEQ ID NO.: 2. In other embodiments, the amino acid sequence of Six-Helix differs from that of SEQ ID NO.: 2 by addition, deletion, substitution or alteration of at least one amino acid residue. Six-Helix protein is useful not only for producing Five-Helix, but also as a negative control in screening for drugs that inhibit membrane fusion.

BRIEF DESCRIPTION OF THE DRAWINGS

The file of this patent contains at least one drawing in color. Copies of this patent with color drawing(s) will be provided by the Patent and Trademark Office upon request and payment of the necessary fee.

FIG. 1A is a schematic of HIV-1 membrane fusion depicting events that promote formation of the gp41 trimer-of-hairpins. The N-terminal fusion peptide of gp41 (red), inaccessible in the native state, inserts into target cell membranes following gp120 interaction with CD4 and coreceptors (not shown). Formation of the prehairpin intermediate exposes the N-terminal coiled coil (gray), the target of C-peptide inhibition. This transient structure collapses into the trimer-of-hairpins state that brings the membranes into close apposition for fusion. FIG. 1B shows the design of the 5-Helix construct. The ribbon diagrams (top) depict the core structure of the trimer-of-hairpins (left and D.C. Chan et al., Cell 89, 263-273 (1997)) and a model of 5-Helix (right). The inner gray helices represent N36 peptides, and the outer blue helices represent C34 peptides. One C-peptide has been removed in the model of 5-Helix and orange lines have been drawn to represent connectivity between the helices. In the design of 5-Helix, the N40 (SEQ ID NO: 3) and C38 (SEQ ID NO: 4) sequences (given in single-letter amino acid code) are alternately linked by short Gly/Ser peptide sequences (gray bars in schematic at bottom (See Example 1).

FIGS. 2A-2D show properties of 5-Helix. FIG. 2A is the circular dichroism (CD) apectrum of 5-Helix (10 µM) at 25° C. The spectrum indicates that the 5-Helix protein adopts >95% of the helical content expected from the design. FIG. 2B is a graphic representation of thermal denaturation of 5-Helix monitored by ellipticity at 222 nm in TBS (filled squares) and in 3.7 M guanidine (Gu)HCl/TBS (open squares). The denaturation observed in the GuHCl solution is >90% reversible. FIG. 2C shows results of nickel (Ni)-NTA precipitation of 5-Helix with a His-tagged C-peptide. Untagged 5-Helix and His-tagged C-peptide (denoted C37-H6) were mixed before Ni-NTA agarose was added in order to precipitate complexes containing C37-H6 (lanes 1 and 5 and Example 4). Addition of excess untagged C-peptide (C34) shifts the 5-Helix molecules from the bound to the unbound fraction (lanes 2 and 6). FIG. 2D is the CD spectra of 5-Helix and C37-H6 before (filled squares) and after (open circles) mixing in a mixing cuvette. The increase in ellipticity at 222 nm upon mixing indicates an interaction between the two species that increases the total helical content (corresponding to an additional 28 helical residues per associated C-peptide).

FIGS. 3A-3C show results of assessment of 5-Helix inhibition of HIV-1 envelope-mediated membrane fusion, as described in Example 2. FIG. 3A shows results of assessment of titration of viral infectivity by 5-Helix (filled squares), 6-Helix (open triangles), and 5-Helix(D4) (open circles), as described in Example 3 and 5 The data represent the mean±SEM of two or more separate experiments. FIG. 3B is a graphic representation of antagonistic inhibitory activities of 5-Helix and C34. The number of syncytia were measured in a cell-cell fusion assay performed in the absence or presence of 5-Helix, C34, or mixtures of 5-Helix and C34 at the indicated concentrations. The $IC_{50}$ values for 5-Helix and C34 in this assay are 13±3 nM and 0.55±0.03 nM, respectively (D. C. Chan et al., Proc. Natl. Acad. Sci. USA 95, 15613-15617 (1998)). Data represent the mean and range of mean of duplicate measurements, except for the control (mean±SEM of five measurements). FIG. 3C shows results of assessment of 5-Helix inhibition of pseudotyped virus containing different HIV-1 envelope glycoproteins. The reported $IC_{50}$ values represent the mean±SEM of three independent experiments.

FIGS. 11A-11C show amino acid sequences of peptides (SEQ ID NOS.: 1-10) of the present invention.

DETAILED DESCRIPTION OF THE INVENTION

Figure 1A:
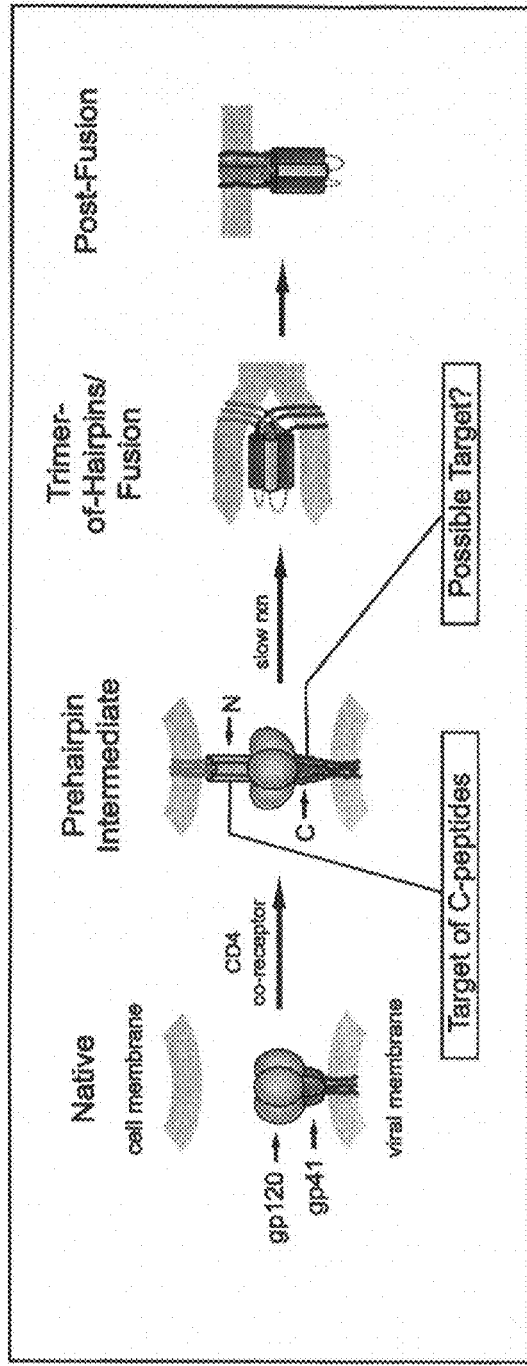
FIGS. 1A and 1B illustrate targeting HIV-1 membrane fusion.
Figure 1B:
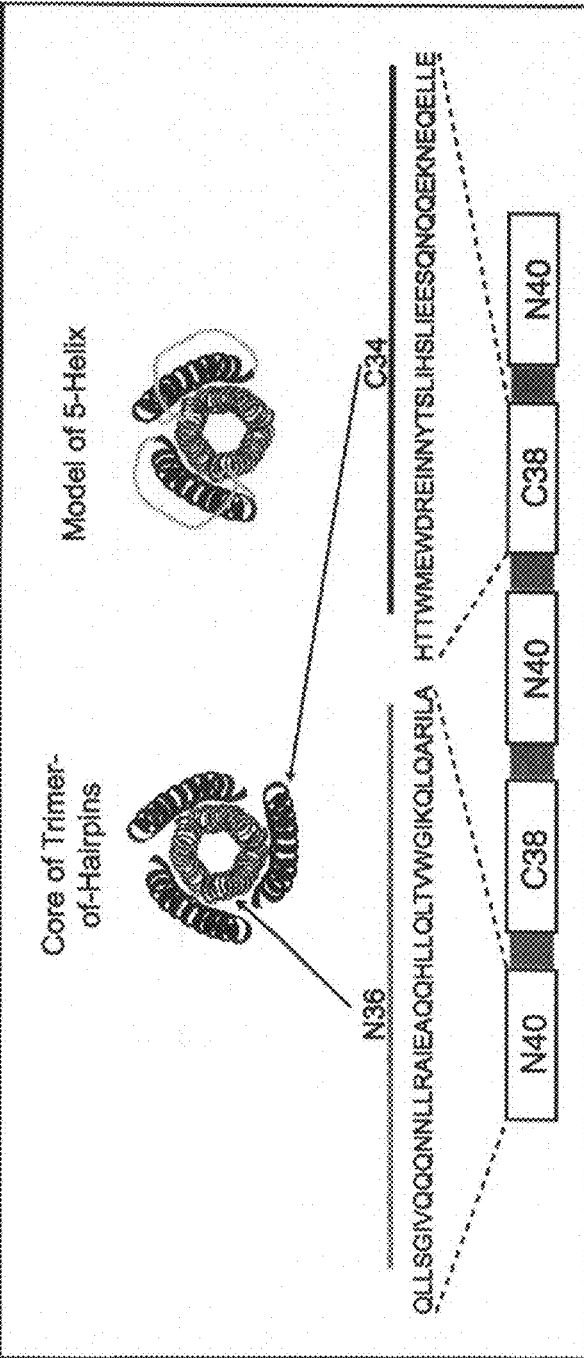

The conformation of a major part of the ectodomain of the gp41 molecule consists of a trimer-of-hairpins structure. The core "trimer-of-hairpins" is comprised of a central three-stranded N-helix coiled coil surrounded by three outer C-helices, forming a bundle with a total of six helices. The trimer-of-hairpins is a common structural element involved in the fusion of many enveloped viruses, suggesting a critical role for this motif in promoting membrane fusion. In HIV gp41, the core of the trimer-of-hairpins is a bundle of six α-helices (formed by the C-terminal regions of three gp41 ectodomains) packed in an antiparallel manner against a central, three-stranded coiled coil (formed by the N-terminal regions of the gp41 molecules) (M. Lu et al., J. Mol. Biol. 290, 1031-1044 (1995); D. C. Chan et al., Cell 89, 263-273 (1997); W. Weissenhorn et al., Nature 387, 426-430 (1997)); K. Tan et al., Proc. Natl. Acad. Sci. USA 94, 12303-12308 (1997). Because the fusion peptide region, which inserts into the cellular membrane, is located at the extreme N-terminus of gp41, and the C-terminal region is adjacent to the transmembrane helix anchored in the viral membrane, the trimer-of-hairpins motif serves to bring the two membranes together. This is illustrated schematically in FIG. 1A. The N-helices (one from each subunit of the trimer) form highly conserved hydrophobic grooves into which the C-helices pack. It is generally agreed that formation of this six-helix structure is required for membrane-fusion to occur.

The importance of trimer-of-hairpins formation for HIV-1 entry led to the hypothesis that the C-terminal region of gp41 might serve as a target for potential membrane-fusion inhibitors. C-peptides have been shown to inhibit HIV-1 entry into cells, with $IC_{50}$ values as low as 1 nM in vitro (C. T. Wild et al., Proc. Natl. Acad. Sci. USA 91, 9770-9774 (1994); D. C. Chan et al., Proc. Natl. Acad. Sci. USA 95, 15613-15617 (1998)). Evidence suggests that C-peptides work in a dominant-negative fashion by binding to the N-peptide region and disrupting trimer-of-hairpins formation. If the C-terminal region is accessible (at least transiently) prior to formation of the trimer-of-hairpins, then it is reasonable to expect that agents that bind to this region of gp41 N-terminal will prevent membrane fusion. Consistent with this notion, peptides derived from the gp41 N-terminal region (referred to as N-peptides) are modest inhibitors of HIV-1 membrane fusion. The inhibitory mechanism of N-peptides has not been determined, in part because these peptides have a strong tendency to aggregate.

Applicants reasoned that a single soluble molecule that contains a folded N-helical core and two of the three C-helices of the core trimer-of-hairpins would be highly stable and would bind a single C-peptide with high affinity. As described herein, the hypothesis that the C-peptide region of gp41 is a target for inhibition of HIV-1 entry has been tested. Results of the assessment, also described herein, have shown that Five-Helix, which binds the C-peptide region of gp41, shows potent inhibitory activity against HIV-1 and against HIV-1 variants containing a diverse set of envelope proteins. These results point to the C-peptide region of HIV gp41 as a viable target to inhibit the formation of the trimer-of-hairpins, which is required for membrane fusion (and, thus, HIV infection of cells) to occur.

Described herein are results that show that a protein that binds to the C-peptide region of gp41 inhibits HIV entry into cells. Such proteins are inhibitors of HIV and serve as the basis for development of additional anti-HIV agents. They might also be used for generating a neutralizing antibody response that targets the N-terminal region of the gp41 ectodomain.

Five-Helix, as the proteins are designated, takes advantage of the binding properties of the N-helix peptide coiled coil while minimizing the tendency of the N-peptides to aggregate. In one embodiment of Five-Helix, five of the six helices that make up the core of the gp41 trimer-of-hairpins structure are connected with (joined by) short peptide linkers. (See FIG. 1A.) In this embodiment, Five-Helix lacks a third C-peptide helix, thus creating a vacancy in order to create a high-affinity binding site for the C-terminal region of gp41. In further embodiments of Five-Helix, the three N-peptide helices and more than two (but less than three complete) C-peptide helices are connected with short peptide linkers. In these embodiments, the three N-peptide helices, two complete C-peptide helices and a portion of the third C-peptide helix are connected with peptide linkers. The portion of the third C-helix can be as few as one amino acid residue of the third C-helix or any number of additional amino acid residues of the helix up to, but not including, all of the amino acid residues of the helix. Five-Helix protein of the present invention is soluble under physiological conditions.

The core of the trimer-of-hairpins, as formed by individual N- and C-peptides, is already quite stable, with a melting temperature of 65° C. Applicants have shown that if 5 of the 6 helices are covalently joined to form a 5-Helix protein, the stability of the core is further increased (the stability is greater than the stability of the 6-Helix core). Under physiological conditions, Five-Helix is folded, soluble, and stable. It has an α-helical content in close agreement with the value predicted from the design. (See FIGS. 2A and 2B.) In affinity-interaction experiments, Five-Helix interacts strongly and specifically with epitope-tagged C-peptides. (See FIG. 2C.) This interaction induces a helical conformation in the bound C-peptide as judged by the difference in circular dichroism before and after mixing. (See FIG. 2D.) These properties are consistent with the intended design of Five-Helix.

Figure 8:
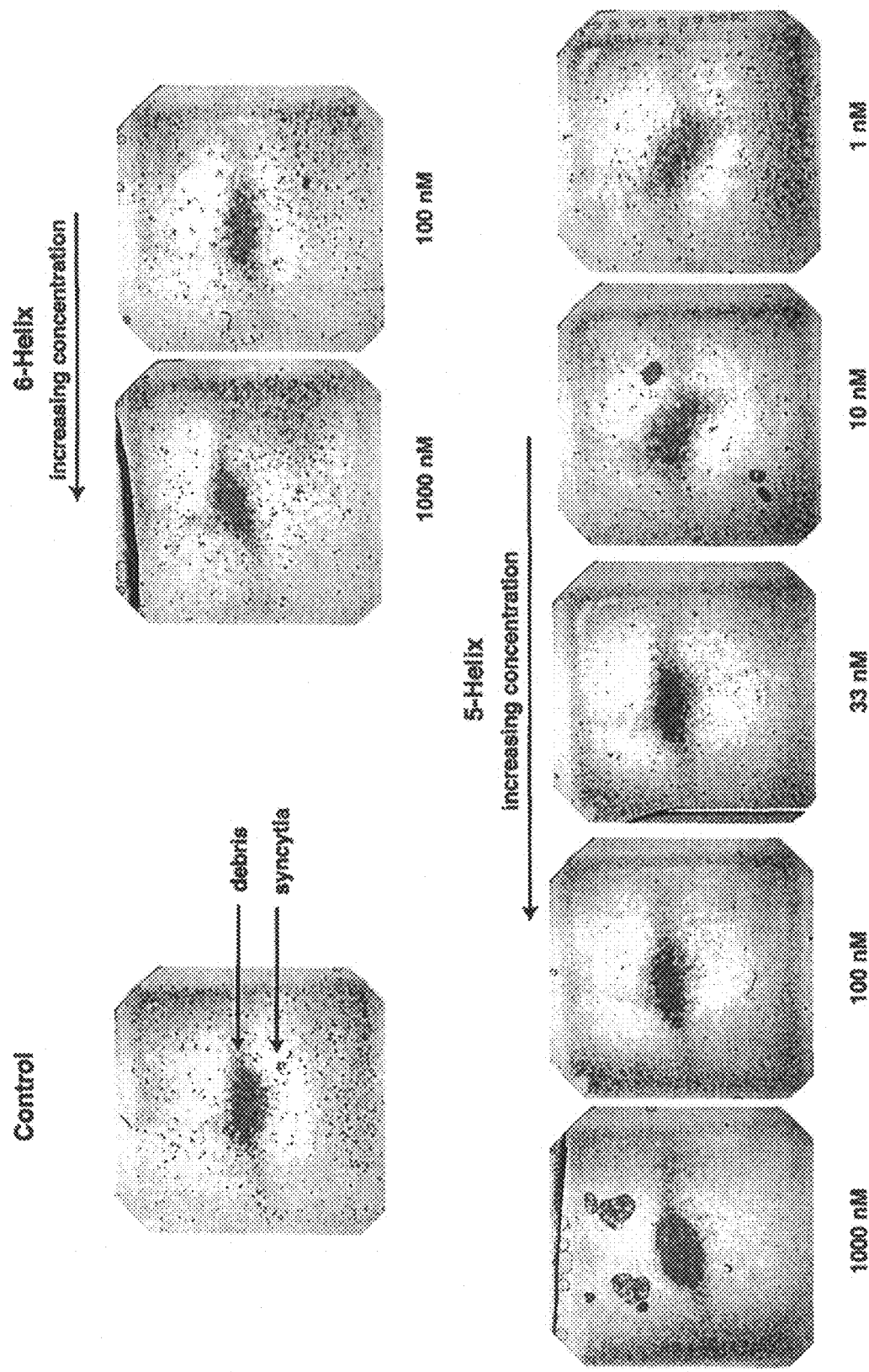
FIG. 8 shows images of cell-cell fusion assay titration experiments. The syncytia (representing fused cells) are blue in the image while debris is brown.
Figure 9:
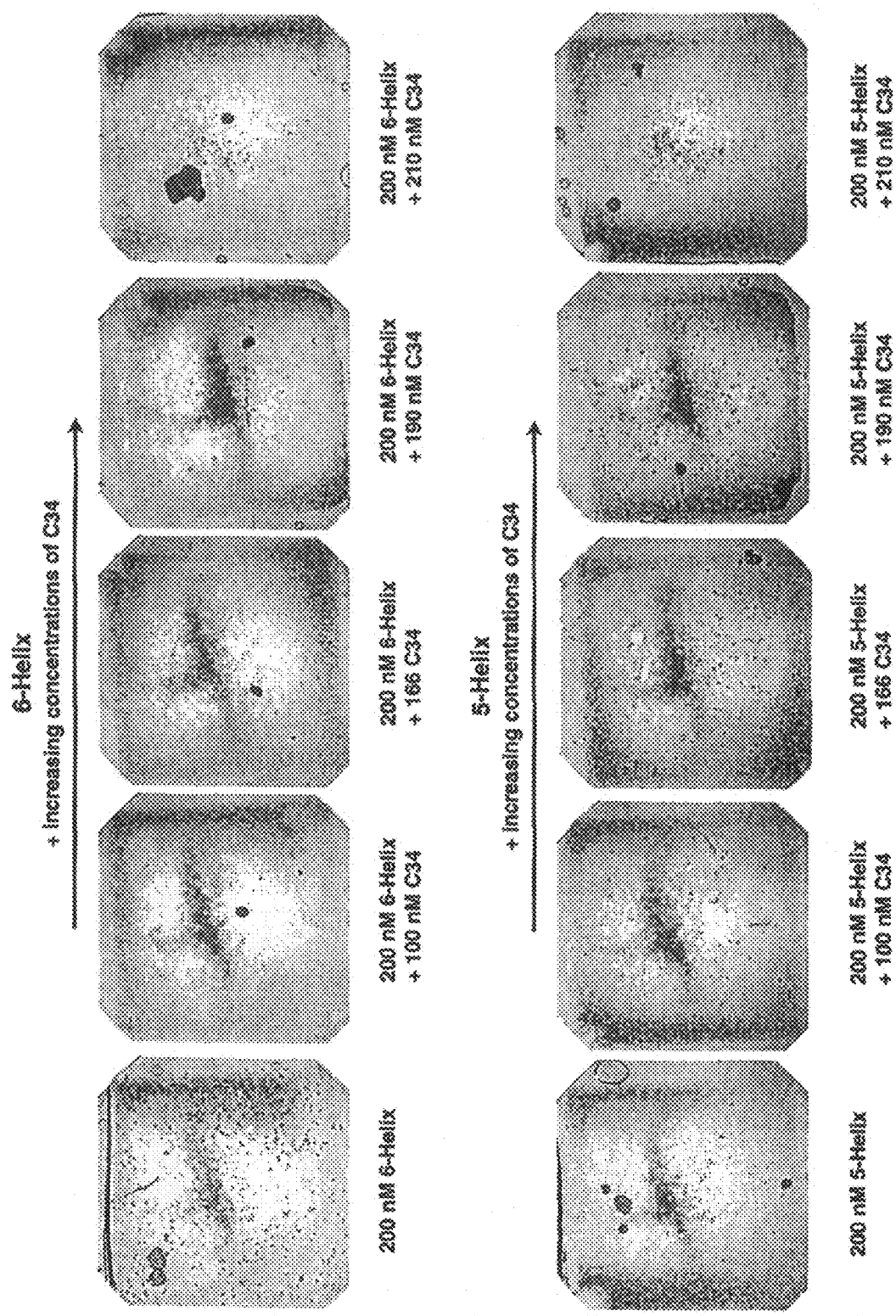
FIG. 9 shows images of cell-cell fusion assay competition experiments. The amount of syncytia are recorded for cultures incubated in 200 nM 6-Helix or 5-Helix with increasing amounts of C34 peptide.
Figure 10:
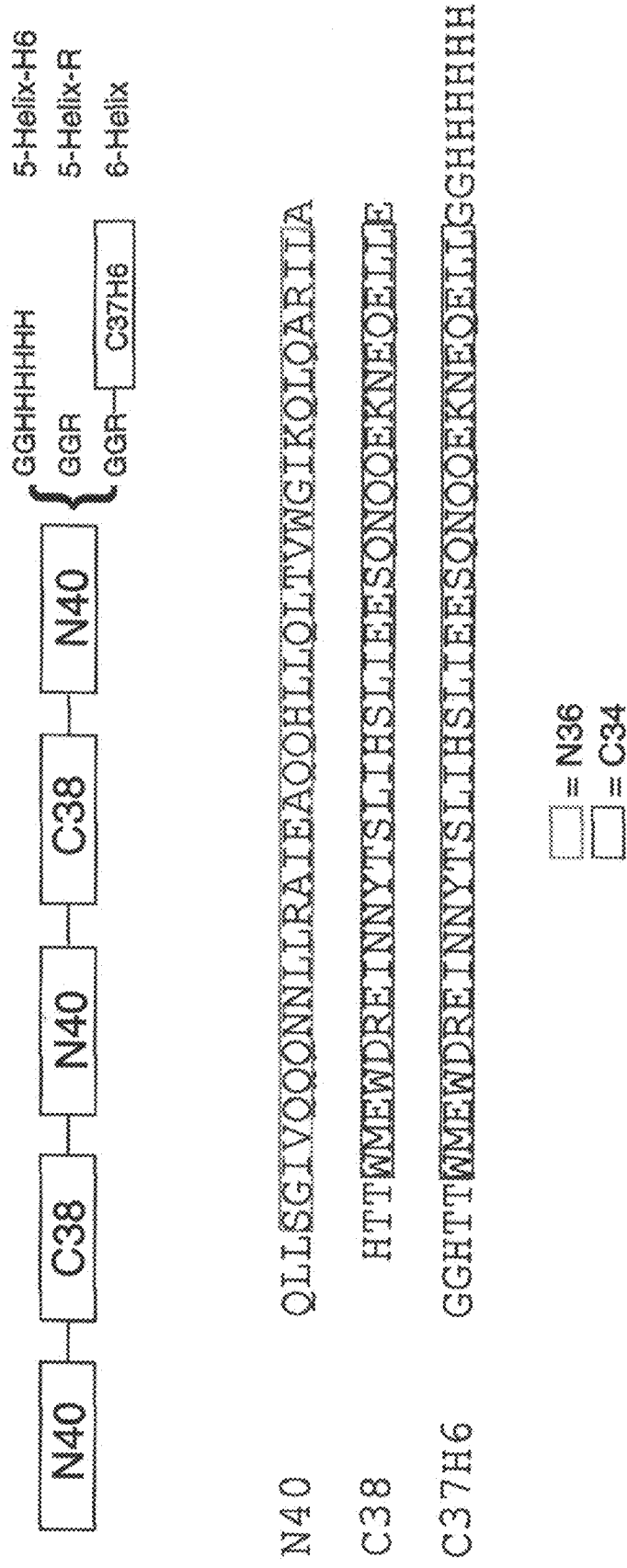
FIG. 10 is a schematic of the design of the Five-Helix constructs. The schematic diagram depicts the linkage pattern of the basic 5-Helix construct. Three different C-termini were added. In 6-Helix, a His-tagged C-peptide is attached to 5-Helix in order to mimic the complete six-helix bundle of the trimer-of hairpins. The N40 and C38 sequences (alternately joined using short Gly/Ser linkers) are derived from the N- and C-peptide regions of HIV HXB2 gp41. (The red- and blue-boxed residues depict the sequences of the N36 (SEQ ID NO.: 11) and C34 (SEQ ID NO.: 12) peptides, respectively.)

Five-Helix potently inhibits HIV-1 membrane fusion (nanomolar $IC_{50}$) as measured by viral infectivity and cell-cell fusion assays. (See FIGS. 3A and 3B.) In contrast, a control protein, denoted Six-Helix, in which the C-peptide binding site is occupied by an attached C-peptide (i.e., all six helices that constitute the gp41 trimer-of-hairpins have been linked into a single polypeptide, as described in Example 1), does not have appreciable inhibitory activity. (See FIG. 3A and FIGS. 8 and 9). Similarly, a Five-Helix variant, denoted Five-Helix(D4), in which the C-peptide binding site is disrupted by mutation of four interface residues (V549, L556, Q563 and V570) to Asp, does not block the membrane fusion event even at 1 μM. (See Example 3 and FIG. 3A.) These results support the conclusion that C-peptide binding is the key determinant of antiviral activity in Five-Helix.

The inhibitory activities of 5-Helix and C-peptides are expected to be antagonistic: when 5-Helix binds C-peptide, the amino acid residues thought to be responsible for the antiviral activities of each inhibitor are buried in the binding interface. Indeed, mixtures of 5-Helix and C34 [a well characterized and potent peptide inhibitor with an $IC_{50}$ of approximately 1 nM] display a dose-dependent antagonistic effect (FIG. 3B). In the presence of 5-Helix, high-potency inhibition by C34 is only observed when the peptide is in stoichiometric excess (FIG. 3B).

Figure 4:
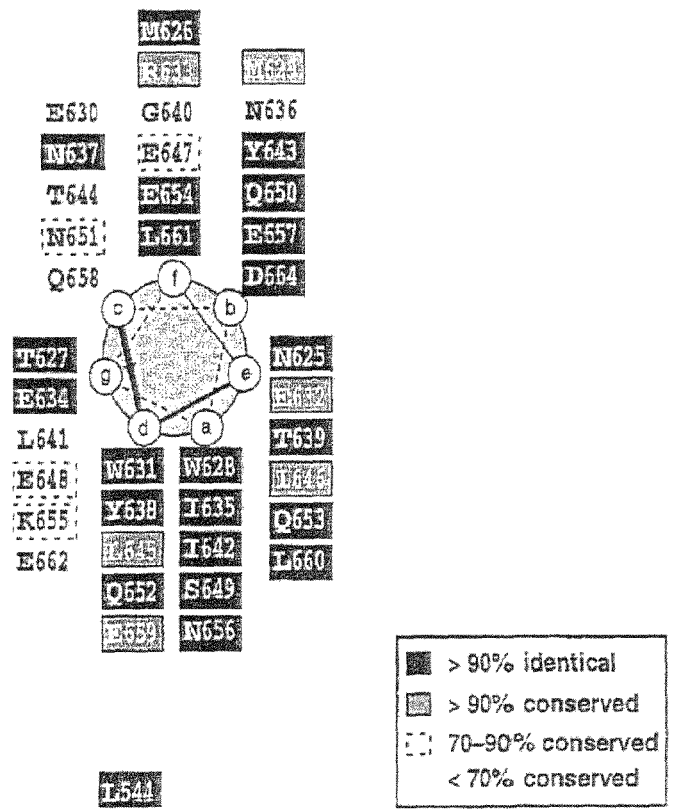
FIG. 4 is a helical wheel diagram depicting the interaction of 5-Helix with the C-peptide region of gp41. The a through g positions in each helix represent sequential positions in the 4,3-hydrophobic heptad repeat in each sequence. The a and d positions in the gp41 C-peptide region interact with the exposed e and g positions on the N40 coiled coil of 5-Helix. Residues are boxed according to their degree of conservation as determined from the alignment of 247 sequences from HIV-1, HIV-2, and SIV isolates (HIV-1 sequence database, August 2000, Los Alamos National Laboratory): black rectangle, >90% identical; grey rectangle, >90% conservative substitution; dotted rectangle, 70-90% conserved; no box, <70% conserved. In generating FIG. 4, substitutions within the following groups of amino acid residues were considered to be conservative: [Asp, Glu], [Lys, Arg], [Asn, Gln], [Phe, Tyr], [Ser, Thr] and [Val, Ile, Leu, Met]. Note the high degree of conservation in the a and d positions of the C-peptide region of gp41, a property markedly lacking in other positions (particularly c and g) of the C-peptide region not directly involved in binding 5-Helix.
Figure 4:
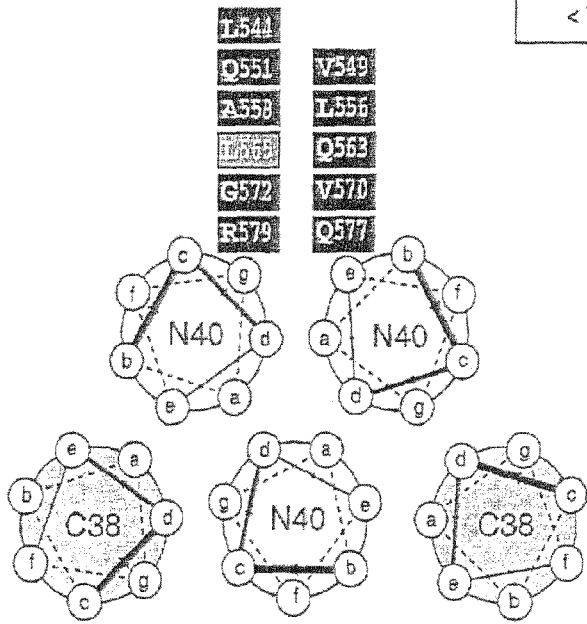
Figure 5:
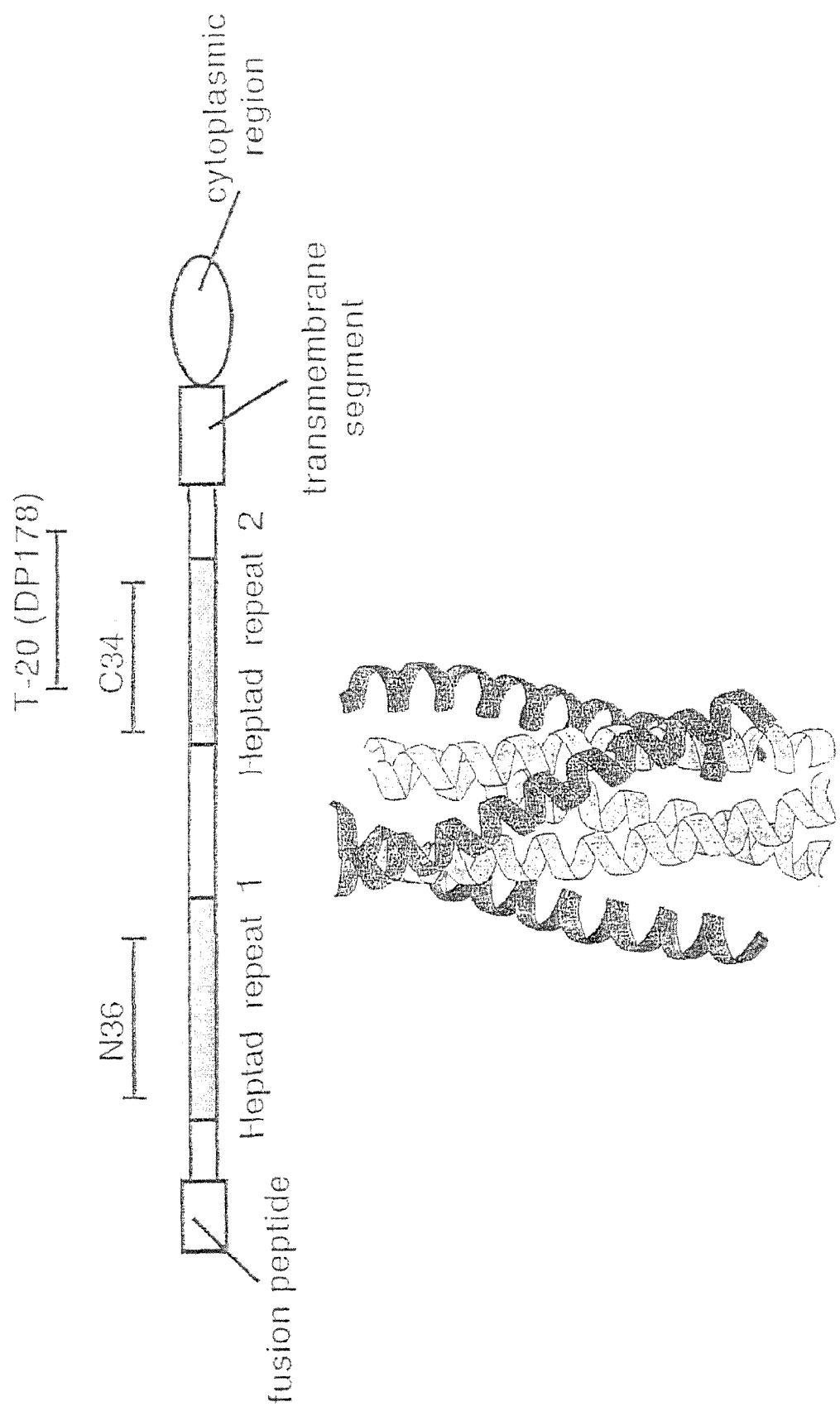
FIG. 5 is the structural arrangement of HIV gp41. Helical regions (heptad repeats) are shown in grey, and the relative position of N—(N36) and C—(C34, DP178) peptides are indicated. In the ribbon diagram of the helical region, the N-peptides are in light grey, while the C-peptide are in dark grey.
Figure 6:
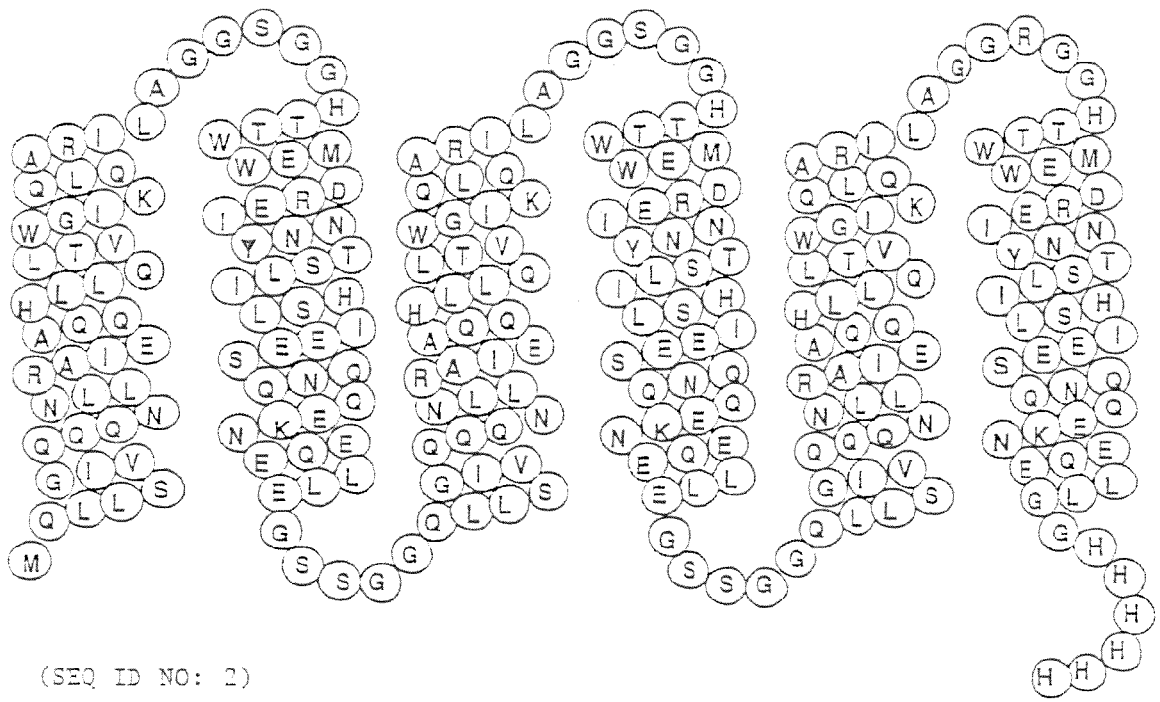
FIG. 6 is the sequence of 6-Helix (SEQ ID NO: 2) and 5-Helix (SEQ ID NO: 1). The predicted helical segments are designated by the stacked sequence.
Figure 6:
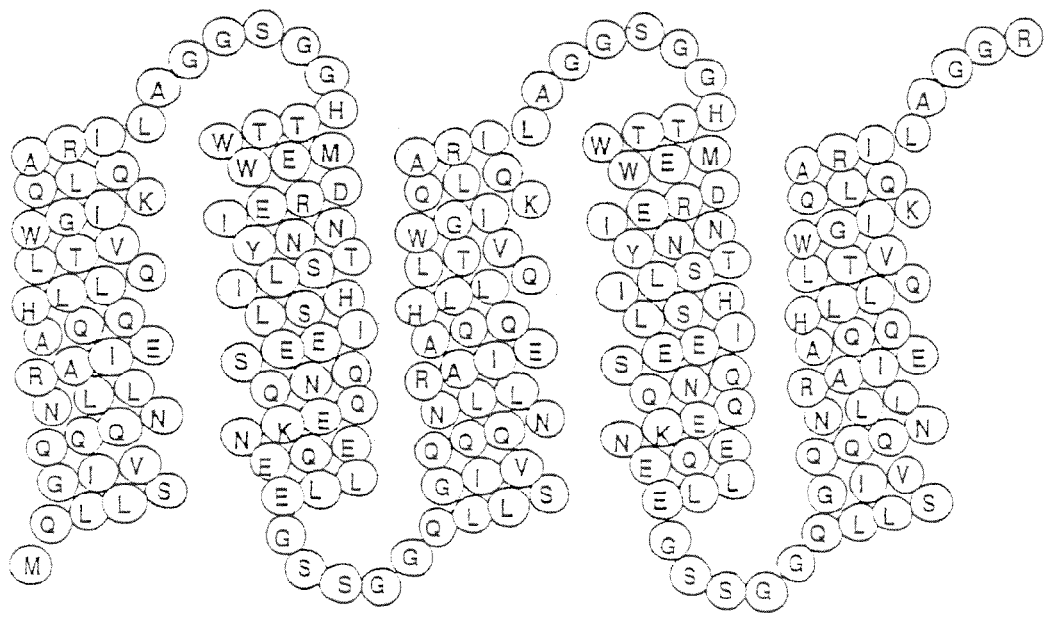
Figure 7:
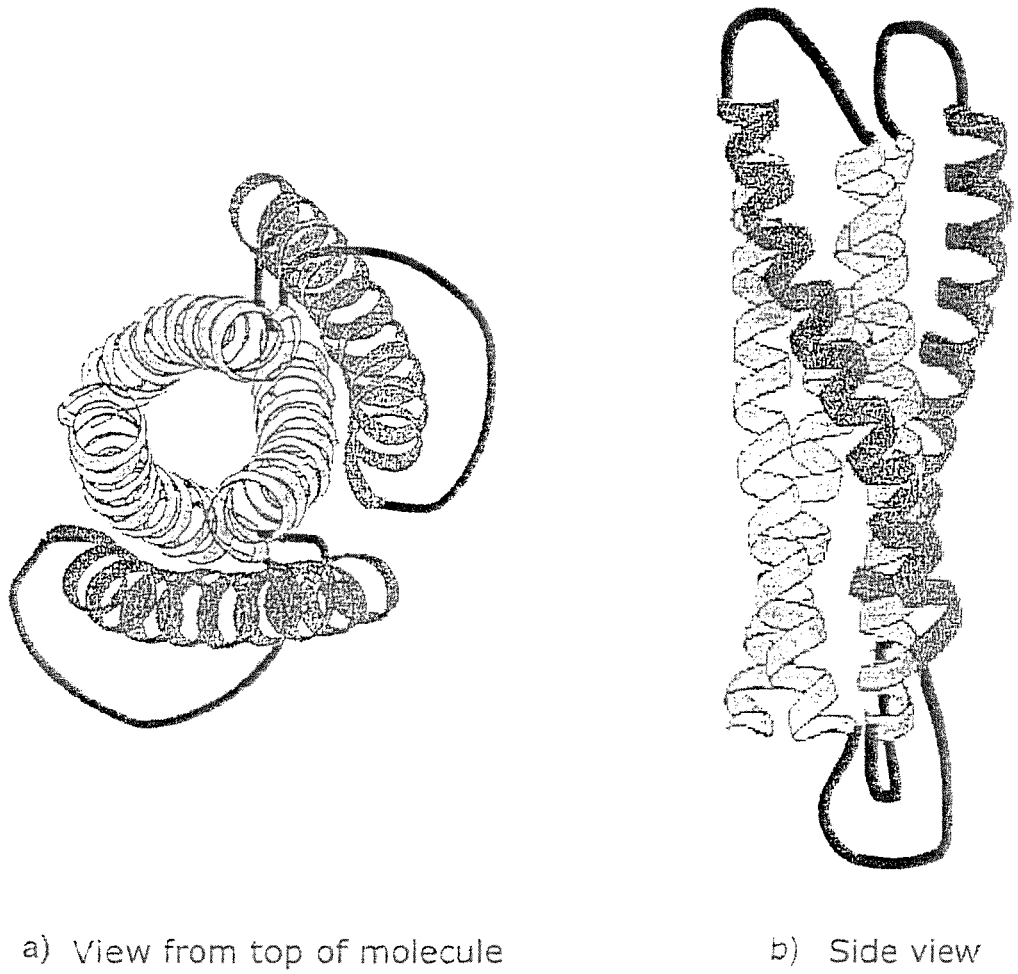
FIG. 7 is a ribbon diagram of one of the possible α-helical arrangements of 5-Helix. The N-helical trimer is light grey, the C-helical regions are in dark grey and the extended loop regions are in black (based on the structure of D. C. Chan, et al. (Cell 89, 263-273 (1997)).

Five-Helix inhibits infection by viruses pseudotyped with a variety of HIV-1 envelope proteins (from clades A, B, and D) with similar potency (FIG. 3D). This broad-spectrum inhibition likely reflects the highly conserved interface between the N- and C-terminal regions within the gp41 trimer-of-hairpins structure (FIG. 4). The residues in the C-peptide region of gp41 that are expected to make contact with 5-Helix are highly conserved in HIV-1, HIV-2, and SIV (FIG. 4).

As a potent, broad-spectrum inhibitor of viral entry, Five-Helix may serve as the basis for the development of a new class of therapeutic agents against HIV-1. Although they typically require parenteral administration, protein-based therapeutics can be practical, as exemplified by insulin, growth hormone, tissue plasminogen activator, granulocyte-colony stimulating factor, and erythropoietin. Alternatively, Five-Helix could be expressed endogenously (e.g., via gene therapy) with secretion into the bloodstream. If Five-Helix were expressed endogenously in HIV-infected cells, it could inhibit intracellular folding and transport of gp160. Five-Helix, Five-Helix (D4), and Six-Helix are also potential reagents for small-molecule drug-screening purposes. Five-Helix offers a great deal of flexibility in the design of variants with better therapeutic characteristics. In principle, Five-Helix can be modified extensively, except at its C-peptide binding site, to alter its immunogenic, antigenic, bioavailability, or inhibitory properties. For example, the C-peptide binding site might be lengthened, shortened, or shifted in the gp41 sequence in order to optimize inhibitory potency by targeting different regions of the gp41 ectodomain.

It would be desirable to generate neutralizing antibodies that mimic the binding properties of Five-Helix. The broadly neutralizing ability of Five-Helix most likely stems from its interaction with the highly conserved residues in the C-peptide region of gp41 (FIG. 4). Unstructured C-peptide immunogens may not elicit broadly neutralizing antibodies because the linear sequence of the gp41 C-peptide region is variable among different HIV-1 strains. Such unstructured C-peptides do not have a long region of conserved amino acids residues. Rather, conserved amino acid residues and nonconserved residues are interspersed. However, constraining C-peptides or C-peptide analogues into a helical conformation (e.g., as in the C-peptide region when it binds Five-Helix) may lead to useful immunogens in the effort to develop an AIDS vaccine. FIG. 4 is a helical wheel diagram depicting the interaction of Five-Helix with the C-peptide region of gp 41. As shown, on the helical wheel, the whole "face" is comprised of conserved or identical amino acid residues. As also shown, there is a high degree of conservation in the a and d positions of the C-peptide region of HIV gp41. Peptides from the C-terminal region of the gp41 ectodomain constrained in such a manner that they present highly conserved amino acid residues on a single face of the molecule (such as in positions a, d and e in FIG. 4) can be produced. They can be used as immunogens to produce antibodies that will presumably bind those amino acid residues in the corresponding unconstrained peptide (C-peptide region of HIV gp41) and, thus, mimic the binding characteristics of Five-Helix. For example, antibodies that bind some or all of the highly conserved (identical and/or conserved) amino acid residues in C38 (see FIG. 4) can be produced. Such antibodies, which mimic the binding of Five-Helix, will work, in effect, as a preventive or vaccine by reducing or preventing the activity (binding) of Five-Helix. Such antibodies to constrained peptides from the C-terminal region of HIV gp41 ectodomain are a subject of this invention.

Intriguingly, the epitope for 2F5, the only known human monoclonal antibody directed against gp41 with broad neutralizing activity, is located immediately C-terminal to the C-peptide region targeted by Five-Helix (T. Muster, et al., J. Virol. 67, 6642-6647 (1993); M. Purtscher, et al., AIDS 10, 587-593 (1996)). The core of the 2F5 epitope (Leu-Asp-Lys-Trp; residues 663-666 in the HIV HXB2 gp 160 sequence) is highly conserved (81% identity) across the same set of HIV-1, HIV-2, and SIV isolates used to generate FIG. 4. However, some HIV-1 escape variants to 2F5 neutralization do not contain mutations in the epitope sequence, suggesting that inhibition by 2F5 may involve recognition of additional determinants. The conformation of the 2F5-bound epitope remains unknown, but antibodies elicited with fragments of gp41 containing this sequence do not possess significant virus-neutralizing activity (T. Muster, et al., J. Virol. 68, 4031-4034 (1994); L. Eckhart, et al., J. Gen. Virol. 77, 2001-2008 (1996)). It remains to be seen if 2F5 inhibits infection by interfering with trimer-of-hairpins formation.

Further, Five-Helix itself is a vaccine candidate. The possibility of eliciting an antibody response against transiently exposed conformations of proteins involved in HIV-1 fusion has been suggested (R. A. LaCasse, et al., Science 283, 357-362 (1999)). One possible well-defined target is the N-terminal coiled coil that is exposed in the prehairpin intermediate (D. M. Eckert, et al., Cell 99, 103-115 (1999)). A 5-Helix-like intermediate may be exposed during the fusion process, and, in this case, antibodies directed against 5-Helix may inhibit viral entry.

Results described herein point to the C-peptide region of HIV-1 gp41 as a viable target to inhibit the formation of the trimer-of-hairpins. Structural and computational methods predict similar trimer-of-hairpins motifs for viruses in many diverse families, including orthomyxoviridae, paramyxoviridae, filoviridae, retroviridae, and others. Moreover, in some of these cases, inhibition of viral entry by peptides analogous to the C-peptides of gp41 has been demonstrated. Thus, the Five-helix design approach may offer a widely applicable strategy for inhibiting viral infections.

In addition, Five-Helix provides a means to study a formed C-peptide binding site in detail, which cannot be done with aggregable N-peptides. The exposed C-peptide binding site in this Five-Helix molecule is useful to identify or design molecules that bind to the N-helical core of gp41 and can be further assessed, using known methods, for their ability to inhibit fusion of the HIV membrane with the membrane of a mammalian cell, such as a human cell, thus inhibiting (reducing or preventing) infection of the cell. Further, Five-Helix can be assessed for its ability to bind to the C-helical region of gp41 and inhibit its function. The N-helical core of gp41 is highly conserved (in terms of amino acid composition) and, thus, it is likely that 5-Helix and variants thereof will be broadly neutralizing against a variety of clinical HIV strains and, thus, useful therapeutically.

The Five-Helix protein, which is based upon the known structure of the gp41 ectodomain, consists, in one embodiment, of three N-peptides and two C-peptides covalently linked and arranged to fold into a substantial part of the N-helical core with two of the three C-helix binding sites occupied by C-peptide. The remaining C-peptide binding site of the N-peptide is exposed. The site exposes an epitope that is 40 amino acids in length. In addition, it is expected that the backbone atoms of the site are rigidly held in a structured conformation, as the N-peptide core is locked into place by the outer two C-peptides.

In single letter amino acid code, the amino acid sequence of one embodiment of Five-Helix is the following:

(SEQ ID NO.: 1)
MQLLSGIVQQQNNLLRAIEAQQHLLQLTVWGIKQLQARILAGGSGGHTTW

MEWDREINNYTSLIHSLIEESQNQQEKNEQELLEGSSGGQLLSGIVQQQN

NLLRAIEAQQHLLQLTVWGIKQLQARILAGGSGGHTTWMEWDREINNYTS

LIHSLIEESQNQQEKNEQELLEGSSGGQLLSGIVQQQNNLLRAIEAQQHL

LQLTVWGIKQLQARILAGGR.

In single letter amino acid code, the amino acid sequence of 6-Helix is the following:

(SEQ ID NO.: 2)
MQLLSGIVQQQNNLLRAIEAQQHLLQLTVWGIKQLQARILAGGSGGHTTW

MEWDREINNYTSLIHSLIEESQNQQEKNEQELLEGSSGGQLLSGIVQQQN

NLLRAIEAQQHLLQLTVWGIKQLQARILAGGSGGHTTWMEWDREINNYTS

LIHSLIEESQNQQEKNEQELLEGSSGGQLLSGIVQQQNNLLRAIEAQQHL

LQLTVWGIKQLQARILAGGRGGHTTWMEWDREINNYTSLIHSLIEESQNQ

QEKNEQELLGGHHHHHH.

Five-Helix protein can be produced by a variety of methods. For example, it can be produced, as described in Example 1, from a larger protein, such as 6-Helix, by enzymatic (trypsin) digestion. Alternatively, it can be produced, using known methods and expression systems, by expressing Five-Helix protein-encoding DNA, which can be a single DNA that encodes the entire Five-Helix protein or two or more DNA "units", each of which encodes a portion (e.g., one or more N helices, one or more C helices) of N-Helix protein. The yield of expression and purification of Five-Helix can be significantly improved by direct expression of the Five-Helix gene in an appropriate host cell, such as E. coli. In this approach, the Five-Helix gene encodes the residues present in the final Five-Helix protein; A C-terminal His-tag can be attached to facilitate purification (with or without a protease cleavage site to later remove the tag). The protein can then be used directly without the proteolytic cleavage and unfolding steps required for producing Five-Helix starting from Six-Helix. This Five-Helix molecule may be expressed as a folded active molecule, allowing its use in biological selections or screens for optimizing its properties. Alternatively, protein synthetic methods can be used to produce Five-Helix protein. The five helices of Five-Helix can be joined covalently (such as by means of a linker of at least one (one or more) amino acid residues) or by other means which results in formation of a protein which is stable under physiological conditions and is correctly folded such that the remaining surface of Five Helix is presented so that it is available to bind C34 peptide. In the embodiments in which there are three N-helices and more than two (but less than three complete) C-helices, the helices can be similarly joined.

Five-Helix can have a wide variety of sequences, both in the N- and C-helix regions and in the linker components, and can be comprised of L-amino acid residues, D-amino acid residues or a combination of both L- and D-amino acid residues. The amino acids residues can be modified. Five-Helix can include amino acid residues in addition to those of the helices and linkers (e.g., to stabilize the molecule). It is likely that the Five-Helix described here can be altered to enhance stability and activity. Minor changes in the design of the loops connecting the N- and C-helices (both in length and composition) and the exact borders of the N- and C-helices are likely to have significant effects on the stability, yield, and activity of Five-Helix.

As currently constructed, Five-Helix exposes a C-peptide binding site encompassing 40 amino acids along the N-helical core. A strategy for exposing shorter segments of the C-peptide binding site on 5-helix (or related molecules) involves attaching a short C-peptide sequence onto the longer exposed epitope. A molecule of this type might aid in the development of drugs targeted specifically to a shorter epitope along the N-helical core. For instance, a single pocket region (similar to that found in IQN17; D. M. Eckert, et al., Cell 99, 103-115 (1999)) could be exposed in Five-Helix by binding a C-peptide that lacks the residues that bind there (the first 10 or so residues of C34). These short C-peptide sequences could be attached to Five-Helix through a variety of means, including covalent crosslinking or merely extending the sequence of Five-Helix to cover part of the exposed epitope.

Five-Helix is useful in a variety of contexts. As described herein, Five-Helix is a potent inhibitor of viral membrane fusion, and, thus, acts on the virus before it enters the cell (unlike current practical therapy) which acts on HIV-infected cells. Five-Helix is soluble and has been shown to be stable under the conditions described herein. It should also be possible to generate 5-Helix variants with an increased molecular weight (by oligomerization or tethering to a large protein) to reduce the rate of kidney clearance. In addition, Five-Helix dimers can be made by disulfide crosslinking, to produce a molecule filtered to a lesser extent than the Five-Helix "monomer". Thus, it is reasonable to expect that dimers might have an enhanced bioavailability when compared to that of the C-peptides.

Five-Helix prevents virus from entering cells, unlike standard therapy that targets viral proteins after viral entry, and thus, Five-Helix can be used prophylactically to prevent infection or reduce the extent to which infection occurs. One use for such a therapeutic is in the event of a needlestick injury, such as might occur in a hospital or in settings in which needles contaminated with HIV are shared. For example, an individual who is stuck with a needle and is or might be infected with HIV can receive a sufficient quantity of Five-Helix (therapeutically effective quantity) in one or more dose(s) in order to prevent or reduce HIV entry into cells. Five-Helix can be administered, for example, by intravenous or intramuscular injection.

In one embodiment of the present invention, Five-Helix is used to reduce HIV infection in an individual. In this embodiment, Five-Helix is administered, either as Five-Helix itself or via expression of Five-Helix-encoding DNA in appropriate host cells or vectors, to an individual in sufficient quantity to reduce (totally or partially) HIV infection of the individual's cells. That is, a dose of Five-Helix sufficient to reduce HIV infection (an effective dose) is administered in such a manner (e.g., by injection, topical administration, intravenous route) that it inhibits (totally or partially) HIV entry into cells. In one embodiment, a gene therapy approach is used to provide the effective dose, by introducing cells that express Five-Helix protein into an individual. Five-Helix can be administered to an individual who is HIV infected to reduce further infection, or to an uninfected individual to prevent infection or reduce the extent to which infection occurs.

Pharmaceutical compositions which comprise Five-Helix in an appropriate carrier (e.g., a physiologically acceptable buffer) are a subject of this invention. They are useful for preventive and therapeutic purposes and can be administered via a variety of routes (e.g., injection, topical administration, intravenous route).

Five-Helix appears to present a single, intact C-helix binding site and, thus, is useful for screening for drugs that inhibit membrane fusion. Five-Helix exposes a larger, more rigid target for potential drug screens than does IQN17. The molecules 6-Helix and 5-Helix(D4) are a useful negative control in these studies.

The Five-Helix exposed epitope can also be used as an antigen for producing antibodies, particularly neutralizing antibodies using known methods. The antibodies can be monoclonal or polyclonal.

The serum stability of Five-Helix can be tested, using known methods, to ascertain its therapeutic potential. If Five-Helix is degraded, the most likely point of attack/degradation is the glycine/serine linker regions. In this case, different linker regions can be generated and tested (see below). The inhibitory ability of these anti-Five-Helix sera and ascites can be tested using standard fusion assays.

The outside surface of Five-Helix can be varied, for example, to enhance bioavailability, decrease toxicity and avoid immune clearance. Since Five-Helix exhibits potent inhibitory activity, whereas the 6-Helix bundle does not, it is the exposed groove, including the pocket region, that is responsible for inhibition. The rest of the molecule simply provides a scaffold for displaying the exposed groove. Therefore, this scaffold can be modified without adversely affecting the inhibitory activity of Five-Helix. Modification of the scaffold may provide several advantages. First, it would facilitate procedures in which multiple administrations of Five-Helix are required. For example, when Five-Helix is used as an anti-HIV therapeutic agent, multiple doses might be required. After extended administration, individuals might develop antibodies to Five-Helix that are likely to increase its clearance from the body. The availability of multiple versions of 5-Helix would help to circumvent this problem by evading pre-existing antibodies. Second, it may be possible to design versions of Five-Helix, for example by introducing glycosylation sites on the external surface, in which the scaffold is less immunogenic. For vaccine studies, this modification would help to bias the immune response toward the exposed groove as opposed to the scaffold.

The observation that binding the gp41 C-helical region prevents HIV infection suggests a strategy for constructing an HIV vaccine. Analogous to inhibition of HIV by C-peptides, Five-Helix likely inhibits gp41 by binding to a fusion intermediate of gp41 called the prehairpin intermediate. Whereas the C-peptide inhibitors function by binding to the N-peptide region of this intermediate, Five-Helix likely functions by binding to the C-peptide region. These considerations strongly suggest that the C-peptide region of gp41 is a good drug target for the development of HIV entry inhibitors. Moreover, it may be possible to use C-peptide-based constructs as immunogens to elicit neutralizing antibodies. In the case of Five-Helix, the target of inhibition is a helical conformation of the C-peptide region, but reagents targeting other conformations of the C-peptide region may also have inhibitory activity.

Recent vaccine studies (R. A. LaCasse, et al., Science 283, 357-362 (1999)) suggest that intermediates of the envelope-mediated fusion process can elicit strongly neutralizing antibodies. Antibodies to such fusion intermediates would target conserved regions of the envelope proteins and therefore would be likely to neutralize a broad range of viral strains. Antibodies to the C-peptide region would target a region that is highly conserved and critical to the fusion process.

The trimer-of-hairpins is a common feature of many viral membrane fusion proteins. It has been observed in crystal structures of Influenza, Ebola, SV5 (simian parainfluenza virus 5), and RSV (human respiratory syncitial virus). In addition, many other members of the retrovirus, paramyxovirus, and filovirus families are predicted to contain this motif A similar structure has been observed in the associated vertebrate vesicle fusion proteins. The basic strategy described herein can be applied to any of these systems in order to inhibit fusion. One subject of this invention is a method of inhibiting formation of the trimer-of-hairpins of an enveloped virus (a virus that comprises a viral envelope protein) by contacting the virus with a drug that binds a viral envelope protein (e.g., the C peptide region of a viral envelope protein) and inhibits formation of the trimer-of-hairpins of the enveloped protein.

The present invention is illustrated by the following examples, which are not intended to be limiting in any way.

Example 1

Production of 5-Helix

The design of 5-Helix was based on the N36/C34 six-helix bundle crystal structure (D. C. Chan, et al., Cell 89, 263-273 (1997)). For the 5-Helix protein, each peptide region was extended (compared with N36 and C34) by three residues on its N-terminus and one residue on its C-terminus, generating the final N40 and C38 segments (representing residues 543-582 and 625-662 of HIV-1 HXB2 gp160, respectively). Three N40 and two C38 segments were joined using a -GGSGG- linker after N40 and a -GSSGG- linker after C38. All constructs include an N-terminal Met for translation initiation. Two distinct 5-Helix proteins that differ only at their C-termini were generated for this study: (i) His-tagged 5-Helix, which ends in GG(H)6, and (ii) untagged 5-Helix, which ends in -GGR. In addition, a third construct, denoted 6-Helix, was generated in which the 5-Helix backbone was connected to the His-tagged C-peptide, C37-H6 (see Example 4), through a trypsin-cleavable linker (-GGR-) (see FIGS. 10 and 11A-11C).

All DNA constructs were assembled from PCR cassettes sequentially cloned into the pAED4 vector [D. S. Doering, P. Matsudaira, Biochemistry 35, 12677-12685 (1996)] using *E. coli* XL1-Blue (recA-strain, Stratagene). All proteins were recombinantly expressed in *E. coli* strain RP3098 grown in 2xYT to an OD (590 nm) between 0.5-0.7 before induction with IPTG (0.4 mM) for 3 hours. Bacterial pellets were resuspended in Tris/NaCl buffers (Qiaexpressionist booklet, March 1999, Qiagen) supplemented with Complete EDTA-free protease inhibitor tablets (Roche), and subsequently frozen at 20° C. until the day of purification. Thawed resuspensions were lysed (sonication or French press) and centrifuged (35,000×g for 30 minutes) to separate the soluble fraction from inclusion bodies.

His-tagged 5-Helix (generated from plasmid p-5HelixH6) was purified directly from the inclusion bodies resuspended in 8 M urea in TBS (50 mM Tris, pH 8.0, 100 mM NaCl) and 10 mM imidazole. The mixture was clarified by centrifugation (35,000×g for 30 minutes) before binding to a Ni-NTA agarose (Qiagen) column at room temperature. Protein was eluted in 6 M urea/TBS/100 mM imidazole in 40 ml (~5 column volumes). The protein was refolded by slow dripping into a one liter, stirred solution of 20 mM Tris (pH 8.0) at room temperature. Refolded protein was then reconcentrated by passage over a Ni-NTA agarose column and eluted with 20 ml (~2 column volumes) of 100 mM imidazole in TBS.

Untagged 5-Helix was produced via proteolysis of 6-Helix (see below) to generate a 5-Helix/C37-H6 complex. Following digestion with trypsin (1:200 weight ratio in TBS at room temperature for 1 hour, Sigma), the 5-Helix/C37-H6 complex was bound to Ni-NTA agarose and washed extensively to remove excess trypsin. The beads were resuspended in 8 M GuHCl/TBS and heated (70° C.) in order to denature the complex. The nonbinding fraction, containing denatured 5-Helix, was sequentially dialyzed into 8 M urea/20 mM Tris, pH 8.0 (4 hours at room temperature) and 4 M urea/20 mM Tris, pH 8.0 (overnight at 4° C.). The protein was loaded onto a DEAE column (Fastflow, Pharmacia) and a reverse urea gradient (4 M to 0 M urea in 20 mM Tris, pH 8.0) was run over 20 column volumes in 4 hours at room temperature. The protein was eluted from the DEAE resin using a NaCl gradient (0 to 300 mM) in 20 mM Tris, pH 8.0 (10 column volumes).

6-Helix (generated from plasmid p-6Helix) was purified directly from the soluble fraction of the bacterial lysate. The solution was passed over Ni-NTA agarose column and eluted with an imidazole gradient (10-250 mM) in TBS over 10 column volumes.

For all proteins, monomers were separated from aggregates by gel filtration (Sephacryl S200 HR or Superdex 75) in TBS. The proteins were >95% pure as judged by SDS-PAGE and can be concentrated to at least 3 mg/ml. The concentrations of all peptides and proteins were determined by absorbance at 280 nm in 6 M GuHCl [H. Edelhoch, Biochemistry 6, 1948-1954 (1967)].

Example 2

Assessment of the Specificity of 5-Helix/C-peptide Interaction and of Inhibition by 5-Helix of Membrane Fusion The specificity of 5-Helix/C-peptide interaction has been tested using a His-tagged C-peptide (C37-H6, independently expressed in *E. coli* and purified through reverse-phase HPLC) and Ni-agarose precipitation. In TBS with 30 µM of C37-H6, 16 µM of 5-Helix is completely precipitated by Ni-agarose. Addition of 150 µM C34 (no His-tag, chemically synthesized and purified over HPLC) substantially reduces the amount of precipitated 5-Helix. The effective competition of C37-H6 and C34 indicates that 5-Helix binds C-peptide in a specific manner. The CD experiments and competitive binding assays suggest that 5-Helix folds into the predicted conformation. That is, the results support the prediction that 5-Helix contains an exposed C-peptide binding site.

Assays were carried out to assess the ability of 5-Helix to interact with the C-region of gp41 and inhibit function of the fusion protein. This inhibition of membrane fusion by 5-Helix and 6-Helix was assessed using a cell-based assay. Proteins 5-Helix and 6-Helix are serially diluted in modified DMEM media with 5% FCS and aliquoted into slide chambers. HELA cells (4×10$^4$) expressing CD4 and coreceptors and containing a β-galactosidase gene under the control of the Tat promoter are added. CHO cells (2×10$^4$) expressing gp160 (precursor protein to gp120/gp41) and Tat are also added. The 400 µl miniculture is incubated at 37° C. for 8 to 24 hours; fused cells (syncytia) will transcribe and translate β-galactosidase. The cells are fixed in gluteraldehyde and exposed to X-gal/Fe solution for one hour. Syncytia that contain β-galactosidase turn blue-green. In this assay, 5-Helix demonstrates a potent inhibition of syncytia formation, with an IC$_{50}$ of 10-20 nM; in one assay the IC$_{50}$ was 13 nM. 6-Helix does not block fusion appreciably even at 1 µM concentrations.

In order to verify the specificity of the 5-Helix exposed epitope as the inhibitory agent and to rule out a contaminant, mixing experiments with C-peptide have been performed. 5-Helix, at 200 nM concentration, is mixed with C34 at 100, 166, 190 and 210 nM. At the concentrations used, free 5-Helix and free C34 should inhibit almost all of the syncytia in the miniculture. In 5-Helix/C34 mixes where C34 is in excess of the 5-Helix (i.e., at 210 nM) syncytia formation is blocked, whereas syncytia formation is partially blocked in the 5-Helix/C34 mixes where C34 concentration is less than that of 5-Helix (FIG. 3B). By contrast, C34 in the presence of 6-Helix blocks all syncytia formation.

The inhibitory potentials of 5-Helix and 6-Helix have been reproduced in viral fusion experiments. HIV, modified to contain a luciferase reporter gene, is mixed with human osteosarcoma (HOS) cells expressing CD4 and coreceptor in the presence of diluted protein for 6 hours at 37° C. The virus solution is replaced, and the HOS culture is incubated 48 hours more in fresh media. Luciferase activity is measured in a luminometer. In this assay, 5-Helix inhibits luciferase activity with an IC$_{50}$ less than 10 nM. Again, 6-Helix shows no appreciable block up to 1 µM (FIGS. 3A and 3C).

Example 3

Design and Assessment of 5-Helix (D4)

In 5-Helix(D4), four highly conserved residues in the C-peptide binding site of His-tagged 5-Helix (Val549, Leu556, Gln563, and Val570) were mutated to Asp in the final (third) N40 segment. The construct [p-5Helix(D4)] was recombinantly expressed and purified in the same manner as the His-tagged 5-Helix. The His-tagged 5-Helix and 5-Helix (D4) proteins have the same ellipticity: for both, $[\theta]_{222}$=−28, 100±1500 deg cm$^2$ dmol$^{-1}$ (~100% of the predicted helical content) at 4° C. in TBS, and both proteins are extremely stable to thermal denaturation (Tm>98° C.) in TBS, as well as to GuHCl chemical denaturation (Cm values ~6 M for 5-Helix(D4); ~7.2 M for the His-tagged 5-Helix) at 25° C. The slightly decreased stability of 5-Helix(D4) likely reflects the low helical propensity and charge of the Asp residues which, in this context, are placed within a predominantly hydrophobic groove on the surface of 5-Helix.

Example 4

His-tagged C-peptide C37-H6

Peptide C37-H6 is a His-tagged C-peptide of the following sequence: GG HTTWMEWDREINNYTSLIHSLIEESQNQQEKNEQELL GHHHHHH (SEQ ID NO.: 5). The peptide is derived from HIV-1 HXB2 residues 625-661 (underlined) and contains the entire C34 sequence (W628 to L661). C37-H6 is produced from the tryptic digestion of a recombinantly expressed construct, p4-NC1.1, consisting of one N40 segment joined to C37-H6 through a -GGR-linker. Following expression, NC1.1 is purified from the soluble fraction of bacterial lysates in the same manner as 6-Helix. Trypsin digestion (same conditions as for untagged 5-Helix) generates C37-H6, which is then purified to homogeneity by reverse phase HPLC using a Vydac C-18 column and a linear gradient of acetonitrile in water containing 0.1% trifluoroacetic acid. The identity of C37-H6 was confirmed by mass spectrometry (MALDI-TOF, PerSeptive).

Like C34, C37-H6 is a potent inhibitor of HIV-1 membrane fusion, with an $IC_{50} \approx 1$ nM in the cell-cell fusion assay.

The data in FIGS. 2A-2D were generated using the untagged version of 5-Helix, but similar results were obtained with the His-tagged version [see Example 3]. The CD (Aviv 62 DS) experiments were performed in TBS buffer unless otherwise stated. In FIG. 2B, the protein concentration was 1 mM for the TBS sample and 0.54 mM for the GuHCl/TBS sample. In FIG. 2D, a quartz mixing cell (Helma) with 1 ml chambers (4.375 mm/chamber pathlength) was utilized. The polypeptides were at a concentration of 5.9 mM (5-Helix) and 6 mM (C37-H6) in 20 mM Tris, pH 8.0/250 mM NaCl before mixing.

The 5-Helix precipitation experiment (FIG. 2C) was performed in 20 ml TBS with 16 mM untagged 5-Helix, 30 mM His-tagged C37-H6, and/or 150 mM C34. The solution was added to 10 ml of Ni-NTA agarose and incubated at room temperature for 10 minutes. After the unbound supernatant was removed, the beads were washed twice with 1 ml TBS and then eluted with 500 mM imidazole. The Ni-bound and unbound samples were run on a 16.5% Tris-Tricine polyacrylamide gel (Biorad) and stained with Gel-code Blue (Pierce).

Example 5

His-tagged 5-Helix

All data in FIGS. 3A-3C were generated using His-tagged 5-Helix (see Example 1). The cell-cell fusion assays (FIG. 3B) were performed as described (D. C. Chan et al., Proc. Natl. Acad. Sci. USA 95, 15613-15617 (1998)). Inhibition of viral infectivity was studied using a recombinant luciferase reporter assay slightly modified from that previously detailed (D. C. Chan, et al., Proc. Natl. Acad. Sci., USA, 95, 15613-15617 (1998)). Briefly, pseudotyped viruses were generated from 293T cells cotransfected with an envelope-deficient HIV-1 genome NL43LucR⁻E⁻ [B. K. Chen, et al., J. Virol. 68, 654-660 (1994)] and one of four gp160 expression vectors: pCMV-HXB2 (D. C. Chan, et al., Proc. Natl. Acad. Sci., USA, 95, 15613-15617 (1998), pEBB-JRFL (kindly provided by B. K. Chen), pSVIII-UG024.2, and pSVIII-RW020.5. The plasmids pSVIII-UG024.2 and pSVIII-RW020.5 were obtained from the NIH AIDS Reagent Program (F. Gao, B. Hahn, and the DAIDS, NIAID) and code for envelope protein from primary HIV-1 isolates. Supernatants containing virus were prepared as previously described (D. C. Chan et al., Proc. Natl. Acad. Sci. USA 95, 15613-15617 (1998)) and used to infect either HOS-CD4 cells (HXB2 and UG024.2) or HOS-CD4-CCR5 cells (JRFL and RW020.5). Cells were obtained from the NIH AIDS Reagent Program (N. Landau). In FIG. 3A, viral infectivity assays were performed in the standard 24-well format (D. C. Chan et al., Proc. Natl. Acad. Sci. USA 95, 15613-15617 (1998)). The data in FIG. 3C were obtained from assays conducted in 96-well format: virus-containing supernatant (10 ml) and media (90 ml) were overlaid onto HOS cells at 50% confluency. Following two days of incubation at 37° C., the cells were harvested in 100 ml lysis buffer (Luciferase Assay System, Promega), of which 10 ml was analyzed per manufacturer's protocol. The $IC_{50}$ values were calculated by fitting the 5-Helix titration data to a Langmuir function [normalized luciferase activity=$1/(1+[5\text{-Helix}]/IC_{50})$].

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of eliciting an immune response to HIV in an individual, comprising introducing, by an appropriate route, a composition comprising a Five-Helix protein and a physiologically acceptable carrier, wherein the Five-Helix protein is soluble under physiological conditions and comprises the three-N-helices and at least two, but not three complete, C-helices of the trimer of hairpin structure of HIV gp41, wherein the component helices are separated by linkers, in a dose sufficient to elicit the immune response in the individual.

2. The method of claim 1, wherein said Five-Helix protein comprises SEQ ID NO: 1.

3. The method of claim 1, wherein said Five-Helix protein comprises SEQ ID NO: 7.

4. The method of claim 1, wherein said Five-Helix protein comprises SEQ ID NO: 9.

* * * * *

SEQUENCE LISTING

<160> NUMBER OF SEQ ID NOS: 12

<210> SEQ ID NO 1
<211> LENGTH: 220
<212> TYPE: PRT
<213> ORGANISM: Artificial Sequence
<220> FEATURE:
<223> OTHER INFORMATION: Five-Helix Protein

<400> SEQUENCE: 1

```
Met Gln Leu Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Gly Gly Ser Gly Gly His Thr
        35                  40                  45

Thr Trp Met Glu Trp Asp Arg Glu Ile Asn Asn Tyr Thr Ser Leu Ile
    50                  55                  60

His Ser Leu Ile Glu Glu Ser Gln Asn Gln Gln Glu Lys Asn Glu Gln
65                  70                  75                  80

Glu Leu Leu Glu Gly Ser Ser Gly Gly Gln Leu Leu Ser Gly Ile Val
                85                  90                  95

Gln Gln Gln Asn Asn Leu Leu Arg Ala Ile Glu Ala Gln Gln His Leu
            100                 105                 110

Leu Gln Leu Thr Val Trp Gly Ile Lys Gln Leu Gln Ala Arg Ile Leu
        115                 120                 125
```

```
Ala Gly Gly Ser Gly Gly His Thr Thr Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Gly Ser Ser Gly
                165                 170                 175

Gly Gln Leu Leu Ser Gly Ile Val Gln Gln Asn Asn Leu Leu Arg
            180                 185                 190

Ala Ile Glu Ala Gln Gln His Leu Leu Gln Leu Thr Val Trp Gly Ile
            195                 200                 205

Lys Gln Leu Gln Ala Arg Ile Leu Ala Gly Gly Arg
210                 215                 220
```

<210> SEQ ID NO 2
<211> LENGTH: 267
<212> TYPE: PRT
<213> ORGANISM: Artificial Sequence
<220> FEATURE:
<223> OTHER INFORMATION: Six-Helix Protein

<400> SEQUENCE: 2

```
Met Gln Leu Leu Ser Gly Ile Val Gln Gln Gln Asn Asn Leu Leu Arg
  1               5                  10                  15

Ala Ile Glu Ala Gln Gln His Leu Leu Gln Leu Thr Val Trp Gly Ile
             20                  25                  30

Lys Gln Leu Gln Ala Arg Ile Leu Ala Gly Gly Ser Gly Gly His Thr
             35                  40                  45

Thr Trp Met Glu Trp Asp Arg Glu Ile Asn Asn Tyr Thr Ser Leu Ile
 50                  55                  60

His Ser Leu Ile Glu Glu Ser Gln Asn Gln Gln Glu Lys Asn Glu Gln
 65                  70                  75                  80

Glu Leu Leu Glu Gly Ser Ser Gly Gly Gln Leu Leu Ser Gly Ile Val
             85                  90                  95

Gln Gln Gln Asn Asn Leu Leu Arg Ala Ile Glu Ala Gln Gln His Leu
            100                 105                 110

Leu Gln Leu Thr Val Trp Gly Ile Lys Gln Leu Gln Ala Arg Ile Leu
            115                 120                 125

Ala Gly Gly Ser Gly Gly His Thr Thr Trp Met Glu Trp Asp Arg Glu
            130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Gly Ser Ser Gly
                165                 170                 175

Gly Gln Leu Leu Ser Gly Ile Val Gln Gln Gln Asn Asn Leu Leu Arg
            180                 185                 190

Ala Ile Glu Ala Gln Gln His Leu Leu Gln Leu Thr Val Trp Gly Ile
            195                 200                 205

Lys Gln Leu Gln Ala Arg Ile Leu Ala Gly Gly Arg Gly Gly His Thr
210                 215                 220

Thr Trp Met Glu Trp Asp Arg Glu Ile Asn Asn Tyr Thr Ser Leu Ile
225                 230                 235                 240

His Ser Leu Ile Glu Glu Ser Gln Asn Gln Gln Glu Lys Asn Glu Gln
                245                 250                 255

Glu Leu Leu Gly Gly His His His His His
            260                 265
```

```
<210> SEQ ID NO 3
<211> LENGTH: 40
<212> TYPE: PRT
<213> ORGANISM: Artificial Sequence
<220> FEATURE:
<223> OTHER INFORMATION: N40 Peptide

<400> SEQUENCE: 3

Gln Leu Leu Ser Gly Ile Val Gln Gln Asn Asn Leu Leu Arg Ala
 1               5                  10                  15

Ile Glu Ala Gln Gln His Leu Leu Gln Leu Thr Val Trp Gly Ile Lys
            20                  25                  30

Gln Leu Gln Ala Arg Ile Leu Ala
        35                  40

<210> SEQ ID NO 4
<211> LENGTH: 38
<212> TYPE: PRT
<213> ORGANISM: Artificial Sequence
<220> FEATURE:
<223> OTHER INFORMATION: C38 Peptide

<400> SEQUENCE: 4

His Thr Thr Trp Met Glu Trp Asp Arg Glu Ile Asn Asn Tyr Thr Ser
 1               5                  10                  15

Leu Ile His Ser Leu Ile Glu Glu Ser Gln Asn Gln Gln Glu Lys Asn
            20                  25                  30

Glu Gln Glu Leu Leu Glu
        35

<210> SEQ ID NO 5
<211> LENGTH: 47
<212> TYPE: PRT
<213> ORGANISM: Artificial Sequence
<220> FEATURE:
<223> OTHER INFORMATION: C37-H6 Peptide

<400> SEQUENCE: 5

Gly Gly His Thr Thr Trp Met Glu Trp Asp Arg Glu Ile Asn Asn Tyr
 1               5                  10                  15

Thr Ser Leu Ile His Ser Leu Ile Glu Glu Ser Gln Asn Gln Gln Glu
            20                  25                  30

Lys Asn Glu Gln Glu Leu Leu Gly Gly His His His His His His
        35                  40                  45

<210> SEQ ID NO 6
<211> LENGTH: 40
<212> TYPE: PRT
<213> ORGANISM: Artificial Sequence
<220> FEATURE:
<223> OTHER INFORMATION: N40** Peptide

<400> SEQUENCE: 6

Gln Leu Leu Ser Gly Ile Asp Gln Gln Asn Asn Leu Asp Arg Ala
 1               5                  10                  15

Ile Glu Ala Gln Asp His Leu Leu Gln Leu Thr Asp Trp Gly Ile Lys
            20                  25                  30

Gln Leu Gln Ala Arg Ile Leu Ala
        35                  40

<210> SEQ ID NO 7
<211> LENGTH: 225
<212> TYPE: PRT
```

<213> ORGANISM: Artificial Sequence
<220> FEATURE:
<223> OTHER INFORMATION: His-tagged 5-Helix

<400> SEQUENCE: 7

```
Met Gln Leu Leu Ser Gly Ile Val Gln Gln Asn Asn Leu Leu Arg
 1               5                  10                  15

Ala Ile Glu Ala Gln Gln His Leu Leu Gln Leu Thr Val Trp Gly Ile
                20                  25                  30

Lys Gln Leu Gln Ala Arg Ile Leu Ala Gly Gly Ser Gly Gly His Thr
                35                  40                  45

Thr Trp Met Glu Trp Asp Arg Glu Ile Asn Asn Tyr Thr Ser Leu Ile
    50                  55                  60

His Ser Leu Ile Glu Glu Ser Gln Asn Gln Gln Glu Lys Asn Glu Gln
65                  70                  75                  80

Glu Leu Leu Glu Gly Ser Ser Gly Gly Gln Leu Leu Ser Gly Ile Val
                85                  90                  95

Gln Gln Gln Asn Asn Leu Leu Arg Ala Ile Glu Ala Gln Gln His Leu
                100                 105                 110

Leu Gln Leu Thr Val Trp Gly Ile Lys Gln Leu Gln Ala Arg Ile Leu
                115                 120                 125

Ala Gly Gly Ser Gly Gly His Thr Thr Trp Met Glu Trp Asp Arg Glu
                130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Gly Ser Ser Gly
                165                 170                 175

Gly Gln Leu Leu Ser Gly Ile Val Gln Gln Asn Asn Leu Leu Arg
                180                 185                 190

Ala Ile Glu Ala Gln Gln His Leu Leu Gln Leu Thr Val Trp Gly Ile
                195                 200                 205

Lys Gln Leu Gln Ala Arg Ile Leu Ala Gly Gly His His His His
                210                 215                 220

His
225
```

<210> SEQ ID NO 8
<211> LENGTH: 225
<212> TYPE: PRT
<213> ORGANISM: Artificial Sequence
<220> FEATURE:
<223> OTHER INFORMATION: 5-Helix (D4)

<400> SEQUENCE: 8

```
Met Gln Leu Leu Ser Gly Ile Val Gln Gln Asn Asn Leu Leu Arg
 1               5                  10                  15

Ala Ile Glu Ala Gln Gln His Leu Leu Gln Leu Thr Val Trp Gly Ile
                20                  25                  30

Lys Gln Leu Gln Ala Arg Ile Leu Ala Gly Gly Ser Gly Gly His Thr
                35                  40                  45

Thr Trp Met Glu Trp Asp Arg Glu Ile Asn Asn Tyr Thr Ser Leu Ile
    50                  55                  60

His Ser Leu Ile Glu Glu Ser Gln Asn Gln Gln Glu Lys Asn Glu Gln
65                  70                  75                  80

Glu Leu Leu Glu Gly Ser Ser Gly Gly Gln Leu Leu Ser Gly Ile Val
                85                  90                  95

Gln Gln Gln Asn Asn Leu Leu Arg Ala Ile Glu Ala Gln Gln His Leu
```

```
                         100                 105                 110
Leu Gln Leu Thr Val Trp Gly Ile Lys Gln Leu Gln Ala Arg Ile Leu
            115                 120                 125
Ala Gly Gly Ser Gly Gly His Thr Thr Trp Met Glu Trp Asp Arg Glu
        130                 135                 140
Ile Asn Asn Tyr Thr Ser Leu Ile His Ser Leu Ile Glu Glu Ser Gln
145                 150                 155                 160
Asn Gln Gln Glu Lys Asn Glu Gln Glu Leu Leu Glu Gly Ser Ser Gly
                165                 170                 175
Gly Gln Leu Leu Ser Gly Ile Asp Gln Gln Asn Asn Leu Asp Arg
            180                 185                 190
Ala Ile Glu Ala Gln Asp His Leu Leu Gln Leu Thr Asp Trp Gly Ile
        195                 200                 205
Lys Gln Leu Gln Ala Arg Ile Leu Ala Gly Gly His His His His
        210                 215                 220
His
225

<210> SEQ ID NO 9
<211> LENGTH: 227
<212> TYPE: PRT
<213> ORGANISM: Artificial Sequence
<220> FEATURE:
<223> OTHER INFORMATION: 5-Helix-H6-GC

<400> SEQUENCE: 9

Met Gln Leu Leu Ser Gly Ile Val Gln Gln Asn Asn Leu Leu Arg
 1               5                  10                  15
Ala Ile Glu Ala Gln Gln His Leu Leu Gln Leu Thr Val Trp Gly Ile
            20                  25                  30
Lys Gln Leu Gln Ala Arg Ile Leu Ala Gly Gly Ser Gly Gly His Thr
        35                  40                  45
Thr Trp Met Glu Trp Asp Arg Glu Ile Asn Asn Tyr Thr Ser Leu Ile
    50                  55                  60
His Ser Leu Ile Glu Glu Ser Gln Asn Gln Gln Glu Lys Asn Glu Gln
65                  70                  75                  80
Glu Leu Leu Glu Gly Ser Ser Gly Gly Gln Leu Leu Ser Gly Ile Val
                85                  90                  95
Gln Gln Gln Asn Asn Leu Leu Arg Ala Ile Glu Ala Gln Gln His Leu
                100                 105                 110
Leu Gln Leu Thr Val Trp Gly Ile Lys Gln Leu Gln Ala Arg Ile Leu
            115                 120                 125
Ala Gly Gly Ser Gly Gly His Thr Thr Trp Met Glu Trp Asp Arg Glu
        130                 135                 140
Ile Asn Asn Tyr Thr Ser Leu Ile His Ser Leu Ile Glu Glu Ser Gln
145                 150                 155                 160
Asn Gln Gln Glu Lys Asn Glu Gln Glu Leu Leu Glu Gly Ser Ser Gly
                165                 170                 175
Gly Gln Leu Leu Ser Gly Ile Val Gln Gln Asn Asn Leu Leu Arg
            180                 185                 190
Ala Ile Glu Ala Gln Gln His Leu Leu Gln Leu Thr Val Trp Gly Ile
        195                 200                 205
Lys Gln Leu Gln Ala Arg Ile Leu Ala Gly Gly His His His His
        210                 215                 220
His Gly Cys
225
```

```
<210> SEQ ID NO 10
<211> LENGTH: 34
<212> TYPE: PRT
<213> ORGANISM: Artificial Sequence
<220> FEATURE:
<223> OTHER INFORMATION: C34 Peptide

<400> SEQUENCE: 10

Trp Met Glu Trp Asp Arg Glu Ile Asn Asn Tyr Thr Ser Leu Ile His
  1               5                  10                  15

Ser Leu Ile Glu Glu Ser Gln Asn Gln Gln Glu Lys Asn Glu Gln Glu
             20                  25                  30

Leu Leu

<210> SEQ ID NO 11
<211> LENGTH: 36
<212> TYPE: PRT
<213> ORGANISM: Artificial Sequence
<220> FEATURE:
<223> OTHER INFORMATION: N36 Peptide

<400> SEQUENCE: 11

Ser Gly Ile Val Gln Gln Gln Asn Asn Leu Leu Arg Ala Ile Glu Ala
  1               5                  10                  15

Gln Gln His Leu Leu Gln Leu Thr Val Trp Gly Ile Lys Gln Leu Gln
             20                  25                  30

Ala Arg Ile Leu
         35

<210> SEQ ID NO 12
<211> LENGTH: 34
<212> TYPE: PRT
<213> ORGANISM: Artificial Sequence
<220> FEATURE:
<223> OTHER INFORMATION: C34 Peptide

<400> SEQUENCE: 12

Trp Met Glu Trp Asp Arg Glu Ile Asn Asn Tyr Thr Ser Leu Ile His
  1               5                  10                  15

Ser Leu Ile Glu Glu Ser Gln Asn Gln Gln Glu Lys Asn Glu Gln Glu
             20                  25                  30

Leu Leu
```